US008778680B2

(12) United States Patent
Saporta et al.

(10) Patent No.: US 8,778,680 B2
(45) Date of Patent: Jul. 15, 2014

(54) STABLE DIFFERENTIATION OF NT2 CELLS

(75) Inventors: Samuel Saporta, Tampa, FL (US); Elise Spencer, Tampa, FL (US); Rania Shamekh, Tampa, FL (US)

(73) Assignee: University of South Florida, Tampa, FL (US)

( * ) Notice: Subject to any disclaimer, the term of this patent is extended or adjusted under 35 U.S.C. 154(b) by 412 days.

(21) Appl. No.: 11/966,427

(22) Filed: Dec. 28, 2007

(65) Prior Publication Data

US 2008/0160614 A1    Jul. 3, 2008

Related U.S. Application Data

(60) Provisional application No. 60/882,330, filed on Dec. 28, 2006.

(51) Int. Cl.
*A61K 35/30* (2006.01)
*G01N 33/48* (2006.01)

(52) U.S. Cl.
USPC ........... 435/375; 435/366; 435/368; 435/377; 435/383

(58) Field of Classification Search
None
See application file for complete search history.

(56) References Cited

PUBLICATIONS

Paquet-Durand et al., Developmental Brain Research, 142: 161-167, Apr. 2003.*
Megiorni et at., Neuroscience Letters, 373:105-109, published Jan. 10, 2005.*
Lee et al., J Neurosci, 6(2):514-521, Feb. 1986.*
Andrews et al., Laboratory Investigation, 50(2):147-162, 1984.*
Sheridan and Maltese, J Molecular Neurosci., 10:121-128, 1998.*
Marchal et al., Society for Neuroscience, Abstract 726.12, Sep. 2002.*
Suslov, O.N., Kukekuv, V.G., Ignatova, T. N., Steindler. D. A., 2002. "Neural stem cell heterogeneity demonstrated by molecular phenotyping of clonal neurospheres." Proc Natl Acad Sci. USA. 99. pp. 14506-14511.
Iacovitti, L., Stull, N. D., Jin, H. 2001. "Differentiation of human dopamine neurons from an embryonic carcinomal stem cell line." Brain Res. 912. pp. 99-104.
Marchal-Victorion, S., Deleyrolle, L., De Weille, J., Saunier, M., Dromard, C., Sandillon, F., Privat, A., Hugnot, J. P. 2003. "The human NTERA2 neural cell line generates neurons on growth under neural stem cell conditions and exhibits characteristics of radial glial cells." Mol Cell Neurosci. 24. pp. 198-213.
Rada, P., Tucci, S., Teneud, L., Paez, X., Perez, J., Alba, G., Garcia, Y., Sacchettoni, S., Del Corrla, J., Hernandez, L. 1999. "Monitoring gamma-aminobutyric acid in human brain and plasma microdialysates using micellar electrokinetic chromatography and laser-induces fluorescence detection." J Chromatogr B Biomed Sci Appl. 735. pp. 1-10.
R. M. Shamekh, D. F. Cameron, N. A. Patel, E. Spencer, L. O. Colina, S. Saporta. 2005. "Differentiated NT2N neurons derived from aggregated NT2 cells not exposed to retinoic acid survive and engraft in the rat striatum." Program No. 329.8. 2005. Abstract Viewer/Itinerary Planner. Washington, DC. Society for Neuroscience. 2005.
E. Spencer, R. Chamekh, D. F. Cameron, L. Colina, S. Saporta. 2005. "NT2N neurons differentiated by cell aggregation stably express multiple neurotransmitters in vitro." Program No. 940.2. 2005. Abstract viewer/Itinerary Planner. Washington, DC. Society for Neuroscience. 200R.
Berglund, et al. 2004. "Characterization of long-term mouse brain aggregating cultures." Evidence for maintenance of neural precursor cells. J. Comp Neurol. 474. 2004. pp. 246-260.
Zigova, T., Barroso, L. F., Willing, A. E., Saporta, S. McGrogan, M. P., Freeman, T. B., Sanberg, P. R. 2000. "Dopaminergic phenotype of hNT cells in vitro." Brain Res. Dev. Brain Res. 122. pp. 87-90.
J. H. Kim. et al. 2002. "Dopamine neurons derived from embryonic stem cells function in an animal model of Parkinson's disease." Nature. 418. 2002. pp. 50-56.
Hartley, R. S., Margulis, M. Fishman, P. S., Lee, V. M., Tang, C. M. 1999. "Functional synapses are formed between human NTera2 (NT2N, hNT) neurons grown on astrocytes." J. Comp. Neurol. 407. pp. 1-10.
P. T. Nelson. et al. 2002. "Clonal human (hNT) neuron grafts for stroke therapy." Neuropathology in a patient 27 months after implantation. Am. J. Pathol. 160. 2002. pp. 1201-1206.
Otero. et al. 2004. "Beta-catenin signaling is required for neural differentiation of embryonic stem cells." Development. 131. 2004. pp. 3545-3557.
S. J. Pleasure and V. M. Lee. 1993. "NTera2 cells." A human cell line which displays characteristics expected of a human committed neuronal progenitor cell. J. Neurosci. Res. 35. 1993. pp. 585-602.

(Continued)

*Primary Examiner* — Daniel E Kolker
*Assistant Examiner* — Stacey N MacFarlane
(74) *Attorney, Agent, or Firm* — Michele L. Lawson; Michael M. McGaw; Smith & Hopen, P.A.

(57) ABSTRACT

A method of differentiating adult stem cells, such as those derived from a teratocarcinoma cell line, the Ntera2/D1 clone (NT2). The developed cells exhibit a stable neurotransmitter phenotype without the required use of growth factors or retinoic acid in differentiation process, which may be difficult to completely remove during commercial production. An identification of specific neurotransmitters is possible in these differentiated NT2-derived neurons (NT2-N) after 30 days in culture or 30 days survival in vivo. The invention includes a method to stably differentiate neuronal stem/precursor cells to a neuronal phenotype for use in cell replacement therapy for neurodegenerative disease, stroke or spinal cord injury. At least four different types of neurons are produced from this method of differentiation: dopaminergic, cholinergic, GABAergic and glutaminergic. Additionally, since the cells are a cancer stem cell prior to differentiation, they may serve as a model system for developing anti-cancer therapies aimed at the cancer stem cell, rather than the more differentiated daughter cell.

4 Claims, 16 Drawing Sheets

(56) References Cited

PUBLICATIONS

Guillemain, I., Alonso, G., Patey, G., Privat, A., Chaudieu, I. 2000. "Human NT2 neurons express a large variety of neurotransmission phenotypes in vitro." J. Comp. Neurol. 422. pp. 380-395.

S. Saporta. et al. 2000. "In vitro and in vivo characterization of hNT neuron neurotransmitter phenotype." Brain Res. Bull. 53. 2000. pp. 263-268.

Shamekh. et al. 2005. "The role of connexin in the differentiation of NT2 cells in Sertoli-NT2 cell tissue construct grown in the rotating wall bioreactor." Exp. Brain Res. 2005. In press.

A. E. Willing. et al. 2002. "Lithium exposure enhances survival of NT2N cells (hNT neurons) in the hemiparkinsonian rat." Eur. J. Neurosci. 16. 2002. pp. 2271-2278.

T. Zigova. et al. 2001. "Apoptosis in cultured hNT neurons." Dev. Brain Res. 127. 2001. pp. 63-70.

Andrews, P. W. 1984. "Retinoic acid induces neuronal differentiation of a cloned human embryonal carcinoma cell line in vitro." Dev. Biol. 103. pp. 285-293.

Brian D. Armstrong, Zhongting Hu, Catalina Abad, Miya Yamamoto, Williams I. Rodriguez, Jennifer Cheng, Jimmy Tam, Rosa P. Gomariz, Paul H. Patterson, and James A. Waschek. 2003 "Lymphocyte regulation of neuropeptide gene expression after neuronal injury." Journal of Neursoscience Res. 74. pp. 240-247. 2003.

Mahmud Bani-Yaghoub, John F. Bechberger, T. Michael Underhill, and Christian C. G. Naus. 1999. "The effects of gap junction blockage on neuronal differentiation of human NTera2/Clone D1 cells." Experimental Neurology. 156. pp. 16-32. 1999.

Alison E. Willing, Agneta I. Othberg, Samuel Saporta, Alex Anton, Stacy Sinibaldi, Stephen G. Poulos, Donald F. Cameron, Thomas B. Freeman, and Paul R. Sanberg. 1999. "Sertoli cells enhance the survival of co-transplanted dopamine neurons." Brain Res. 822. pp. 246-250. 1999.

Zigova T., Barroso L.F., Willing A.E., Saporta S., McGrogan M.P., Freeman T.B., Sanberg P.R. 2000. "Dopaminergic phenotype of hNT cells in vitro." Brain Res Dev Brain Res. Jul. 30, 2000 122. 1 pp. 87-90.

Miyazono M., Nowell P.C., Finan J.L., Lee V.M., Trojanowski J.Q. 1996. "Long-term integration and neuronal differentiation of human embryonal carcinoma cells (NTera-2) transplanted into the caudoputamen of nude mice." J Comp Neurol. Dec. 23, 1996 376.4 pp. 603-613.

Castelo-Branco G., Wagner J., Rodriguez F.J., Kele J., Sousa K., Rawal N., Pasolli H.A., Fuchs E., Kitajewski J., Arenas E. 2004. "Differential regulation of midbrain dopaminergic neuron development by Wnt-1, Wnt-3a, and Wnt-5a." Proc Natl Acad Sci U S A. Oct. 28, 2003 10. 22. pp. 12747-12752.

\* cited by examiner

STABLE DIFFERENTIATION OF NT2 CELLS

CROSS REFERENCE TO RELATED APPLICATIONS

This application claims priority to currently pending U.S. Provisional Patent Application 60/882,330, entitled, "Stable Differentiation of Adult Stem Cells", filed Dec. 28, 2006, the contents of which are herein incorporated by reference.

FIELD OF INVENTION

This invention relates to use of embryonic and adult stem cells for cell replacement therapy and the treatment of disease.

BACKGROUND OF THE INVENTION

An enormous amount of interest has been generated in the use of embryonic and adult stem cells for cell replacement therapy and the treatment of disease. The most interest has been generated by embryonic stem cells, whose pleuripotent potential enables them to become any tissue in the body. The mechanisms through which embryonic stem cells differentiate have partially been discovered. However, the appropriate concentration and time of delivery of known growth factors have not been adequately determined. Additionally, it is not known if all appropriate growth factors for a given stem cell have been identified.

The use of adult stem cells has also generated a great deal of interest. Adult stem cells are multipotent, rather than pleuripotent. In other words, they are capable of transforming into a variety of tissue types. They can be used in a similar manner to embryonic stem cells, such as for cell replacement therapy and treatment of disease. Interest in adult stem cells and their differentiation has also increased due to a relatively new theory hypothesizing that cancers contain abnormal adult stem cells that are less susceptible to chemotherapy than the more metabolically active progeny of these cancer stem cells. Therefore, new methods of treating cancer should target the proliferation and differentiation of cancer stem cells, as well as reducing the already differentiated cells.

One major problem in studying either the differentiation of embryonic, adult or cancer stem cells is that the differentiation of daughter cells created following division of the stem cells is not stable. These daughter cells often retain a specific cell phenotype for a few days or a few months, and then fail to show the appropriate chemical composition or morphology. This is especially true with attempts to create neurons from embryonic or adult stem cells. While there are numerous reports of the creation of cells with specific neural markers and neurotransmitter phenotypes, usually with the addition of growth factors or retinoic acid to aid differentiation, often these cells fail to maintain their original neurotransmitter phenotype after a few days in culture or following transplantation into the nervous system.

Embryonal carcinoma cells derived from teratocarcinoma contain pleuripotent stem-like cells capable of differentiating into a variety of cell types, including neural cells. Human embryonal carcinomas may be an alternative cell source of adult stem cells. One of the most promising embryonal carcinomas cell source is the Ntera2/D1 (NT2) cell line. The NT2 cell line is derived from an embryonal teratocarcinoma cell line capable of differentiating into post-mitotic dopaminergic neurons (NT2N) following treatment with retinoic acid (RA). RA differentiated NT2N neurons (i.e., hNT neurons) have been shown to engraft within the central nervous system and have been used successfully in ameliorating the behavioral deficits associated with stroke, spinal cord injury, and traumatic brain injury. Although, these cells are derived from teratocarcinoma cells, they do not form tumors in the striatal environment. However, RA differentiation results in an unstable dopaminergic phenotype, leading to the rapid loss of their dopaminergic phenotype. Additionally, RA-induced differentiation of NT2 cells leads to increased apoptosis of differentiated hNT neurons compared to undifferentiated NT2 cells.

Cell aggregation in suspension culture has a profound effect on growth and differentiation of cells. The use of embryonic stem cell suspension cultures that form embryoid bodies, has proven to be valuable method to study lineage commitment and differentiation of pleuripotent stem cells without the influence exerted by surrounding tissue. Suspension cultures of neural stem cells, which form neurospheres, also have proven to be an important method to study proliferation, multipotent differentiation of neural stem cells, and differentiation of neural progenitors. Similarly, teratocarcinomas form embryoid bodies, and have been used as in vitro models to study differentiation and stem cell development. Cell aggregation can influence differentiation and cell fate determination of embryonal carcinoma P19 cells. It was found that a neuronal phenotype was the most abundant phenotype among aggregated mouse embryonic cells, followed by astrocytes and microglia. Recent studies showed that aggregated NT2 cells form spheres that contain cells with neuronal morphology after RA treatment. Additionally, these spheres generate neurons when they are exposed to growth factors that also stimulate neural stem cells. The distinctive feature of cell aggregation is the three-dimensional arrangement of the cells that creates cell-to-cell interaction resembling a normal cell environment in vivo. It was shown that cell to cell contact can activate signaling pathways such as the protein kinase C (PKC) pathway. However, as mentioned above, these cultures required the use of RA and/or growth factors to achieve these results. Use of RA and growth factors can be undesirable due instability issues with the resulting cells, residual RA and growth factors in the cultures, apoptosis concerns and other issues surrounding the use of these compounds.

What is needed is cell that retains its differentiated phenotype for an extended period of time. It would be highly desirable for the methodology used to produce such cells to avoid the use of RA and/or growth factors for development and differentiation of the cells. It would also be desirable to have a cell line that retains the dopaminergic phenotype. The present invention solves this and other important needs as will be evident in the specification below.

SUMMARY OF THE INVENTION

In accordance with the invention, the problem of the unstable phenotype and residual RA in the resulting cells is solved by a method of differentiation using cell aggregation and subsequent substrate contact without requiring the use of RA or exogenous growth factors. By way of example, the method involves growing precursor adult stem cells, such as NT2 cells, in suspension culture for a period of around 7 days or longer in the absence of RA. The cells can then be plated on surfaces such as laminin or PLL and grown as plated cells. The inventors have discovered that, using such methodology, it is possible to develop a cell that retains its differentiated phenotype for an extended period of time.

In a first aspect the present invention provides a method for the stable differentiation of adult stem cells. The method includes the steps of expanding precursor cells in conventional culture, lifting the expanded precursor cells, growing the lifted precursor cells in suspension culture for at least about 7 days, plating the cells on laminin or PLL and growing the plated cells for about 14 days. By "stable differentiation" it is meant that the resulting cells maintain their differentiated phenotype for an extended period of time. In contrast, cells differentiated using techniques such as RA treatment lose their differentiated phenotype after a period of about 3 days. For example, these RA treated cells are initially TH+, but after about 3 days lose this TH+ phenotype. Cells differentiated according to the present invention maintain their phenotype past 3 days, 7 days, 10 days, 14 days, 21 days and out to periods of 30 days or more.

In certain embodiments the precursor cell is an embryonal carcinoma cell. The embryonal carcinoma cell can be derived from a teratocarcinoma line. Alternatively, the precursor cell can be derived from a neuroblastoma line. Furthermore, the precursor cell can be an NT2 cell. In certain embodiments the lifted adult stem cells are grown in suspension culture for at least about 5 days, at least about 7 days, at least about 11 days or at least about 14 days. In an advantageous embodiment, the lifted adult stem cells are grown in suspension culture for at least about 7 days or at least about 11 days. In a particularly advantageous embodiment, the lifted adult stem cells are grown in suspension culture for at least about 14 days. In further embodiments, the lifted adult stem cells are grown in suspension culture for up to about 21 days.

In certain embodiments the plated cells are grown for at least about 5 days, at least about 7 days, at least about 11 days or at least about 14 days. In still further embodiments the plated cells are grown for about 14 days. In an advantageous embodiment, the plated cells are grown for at least about 7 days or at least about 11 days. In a particularly advantageous embodiment, the plated cells are grown for at least about 14 days. Plating the cells provides an adherent surface upon which the cells can grow. Adherent surfaces for plating include laminin, poly-L-lysine (PLL) or DLL. Upon plating, the cells evidence migration and other characteristics of neurons. In practice, the plated cells will, in effect, actually be being "replated" following growth in suspension culture, to the extent that the cells were originally expanded in conventional cultures on plates and then lifted for growth in the suspension culture.

The cells grown in suspension culture can be grown in the absence of retinoic acid in certain embodiments. Additionally, the cells are grown in suspension culture in can be grown in the absence of growth factors. By the phrase "absence of growth factors" it is meant that no additional growth factors will be added to media in which the cells are grown, excluding factors typically found in the serum, which serum the cells require for growth. The growth factors could be further referred to as "exogenous growth factors." Examples of such exogenous growth factors would be egh and fgh. In further embodiments the cells are grown in suspension culture in the absence of both retinoic acid and growth factors. Additionally, the cells do not require conditions of micro-gravity to achieve the desired differentiation.

In a second aspect the present invention provides a method for the stable differentiation of adult stem cells to a neuronal phenotype. The method includes the steps of growing precursor cells in suspension culture for at least about 5 days, plating the cells and growing the plated cells for at least about 7 days.

In certain embodiments the precursor cell is an embryonal carcinoma cell. The embryonal carcinoma cell is derived from a line selected from the group consisting of teratocarcinoma line and a neuroblastoma line. Furthermore, the precursor cell can be an NT2 cell.

In certain embodiments the precursor cells are grown in suspension culture for at least about 5 days, at least about 7 days, at least about 11 days or at least about 14 days. In an advantageous embodiment, the precursor cells are grown in suspension culture for at least about 7 days or at least about 11 days. In a particularly advantageous embodiment, the precursor cells are grown in suspension culture for at least about 14 days. In further embodiments, the precursor cells are grown in suspension culture for up to about 21 days.

In certain embodiments the plated cells are grown for at least about 5 days, at least about 7 days, at least about 11 days or at least about 14 days. In still further embodiments the plated cells are grown for about 14 days. In an advantageous embodiment, the plated cells are grown for at least about 7 days or at least about 11 days. In a particularly advantageous embodiment, the plated cells are grown for at least about 14 days. Plating the cells provides an adherent surface upon which the cells can grow. Adherent surfaces for plating include laminin, poly-L-lysine (PLL) or DLL.

The cells grown in suspension culture can be grown in the absence of retinoic acid in certain embodiments. Additionally, the cells are grown in suspension culture in can be grown in the absence of growth factors. In further embodiments the cells are grown in suspension culture in the absence of both retinoic acid and growth factors. Additionally, the cells do not require conditions of micro-gravity to achieve the desired differentiation.

In a third aspect the present invention provides a method for the differentiation of adult stem cells to a neuronal phenotype. The method includes the steps of culturing the precursor adult stem cells as three-dimensional spheres for at least about 5 days, plating the cells, and growing the plated cells. The phrase "culturing the precursor cells as three-dimensional spheres" refers to the conditions where the cells are able to group or cluster together much as aggregates, free of the constraints imposed by growth of cells adjacent to a fixed surface such as that found when cells are grown on plates. Cell aggregation is one such technique whereby the cells are able to grow in 3-dimensions, with an environment analogous to that which would be found in vivo, as opposed to 2-dimensional plate growth.

In certain embodiments the precursor cell is an embryonal carcinoma cell. The embryonal carcinoma cell can be derived from a line selected from the group consisting of teratocarcinoma line and a neuroblastoma line. Furthermore, the precursor cell can be an NT2 cell.

In certain embodiments the precursor cells are grown in suspension culture for at least about 5 days, at least about 7 days, at least about 11 days or at least about 14 days. In an advantageous embodiment, the precursor cells are grown in suspension culture for at least about 7 days or at least about 11 days. In a particularly advantageous embodiment, the precursor cells are grown in suspension culture for at least about 14 days. In further embodiments, the precursor cells are grown in suspension culture for up to about 21 days.

In certain embodiments the plated cells are grown for at least about 5 days, at least about 7 days, at least about 11 days or at least about 14 days. In still further embodiments the plated cells are grown for about 14 days. In an advantageous embodiment, the plated cells are grown for at least about 7 days or at least about 11 days. In a particularly advantageous embodiment, the plated cells are grown for at least about 14 days. Plating the cells provides an adherent surface upon which the cells can grow. Adherent surfaces for plating include laminin, poly-L-lysine (PLL) or DLL.

The cells grown in suspension culture can be grown in the absence of retinoic acid in certain embodiments. Additionally, the cells are grown in suspension culture in can be grown in the absence of growth factors. In further embodiments the cells are grown in suspension culture in the absence of both retinoic acid and growth factors. Additionally, the cells do not require conditions of micro-gravity to achieve the desired differentiation.

In a fourth aspect the present invention provides a method for the stable differentiation of Ntera2/D1 (NT2) cells to a neuronal phenotype. The method includes the steps of expanding NT2 cells in conventional culture, lifting the expanded NT2 cells, growing the lifted NT2 cells in suspension culture for at least about 7 days, plating/replating the cells growing the replated cells. Cells differentiated according to the present invention maintain their phenotype past 3 days, 7 days, 10 days, 14 days, 21 days and out to periods of 30 days or more.

In certain embodiments the lifted NT2 cells are grown in suspension culture for at least about 5 days, at least about 7 days, at least about 11 days or at least about 14 days. In an advantageous embodiment, the lifted NT2 cells are grown in suspension culture for at least about 7 days or at least about 11 days. In a particularly advantageous embodiment, the lifted NT2 cells are grown in suspension culture for at least about 14 days. In further embodiments, the lifted NT2 cells are grown in suspension culture for up to about 21 days.

In certain embodiments the replated cells are grown for at least about 5 days, at least about 7 days, at least about 11 days or at least about 14 days. In still further embodiments the replated cells are grown for about 14 days. In an advantageous embodiment, the replated cells are grown for at least about 7 days or at least about 11 days. In a particularly advantageous embodiment, the replated cells are grown for at least about 14 days.

The NT2 cells grown in suspension culture can be grown in the absence of retinoic acid in certain embodiments. Additionally, the cells are grown in suspension culture in can be grown in the absence of growth factors. In further embodiments the cells are grown in suspension culture in the absence of both retinoic acid and growth factors.

The present invention further provides differentiated stem cells. The differentiated stem cells can be produced according to any of the methods of the present invention.

We have developed an alternate method of differentiation using cell aggregation and subsequent substrate contact without the use of RA or exogenous growth factors. The developed a method of differentiating adult stem cells can use cells derived from a teratocarcinoma cell line, such as the Ntera2/D1 clone (NT2). NT2 line is a cell line that is available from ATCC. Using the methodology of the invention the NT2 cells or other cell line differentiates to neurons with a stable neurotransmitter phenotype without the use of growth factors or retinoic acid, which may be difficult to completely remove during commercial production. We are able to identify specific neurotransmitters in these differentiated NT2-derived neurons (NT2-N) after 30 days in culture or 30 days survival in vivo.

The resulting stably differentiated neuronal stem/precursor cells exhibit a neuronal phenotype that can be then be used in cell replacement therapy for neurodegenerative disease, stroke or spinal cord injury. At least four different types of neurons are produced from this method of differentiation: dopaminergic, cholinergic, GABAergic and glutaminergic. Additionally, since the cells are a cancer stem cell prior to differentiation, they may serve as a model system for developing anti-cancer therapies aimed at the cancer stem cell, rather than the more differentiated daughter cell.

The inventors have also discovered that it is possible to develop a stable dopaminergic neuronal cell that is tyrosine hydroxylase (TH) positive, and continues to express TH in vitro, and in vivo following transplantation. Our data evidence that NT2N neurons differentiated in NT2 spheres without RA express a stable dopaminergic phenotype. Our data also implicate the involvement of β-catenin/GSK-3β in the differentiation of NT2 cells to NT2N neurons in NT2 spheres.

The present invention provides a stable dopaminergic neuronal cell that is tyrosine hydroxylase (TH) positive, and continues to express TH in vitro, and in vivo following transplantation. The methodology has enabled an examination of the pathway or pathways involved for the differentiation of NT2 cells, and the degree to which their differentiation mimicked the differentiation process of dopaminergic neurons. A distinctive feature of cell aggregation is the three-dimensional arrangement of cells that recreates cell-to-cell interaction more closely resembling the normal cell environment in vivo in which neurons differentiate and develop. Similarly, the Wnt signaling pathway plays a critical role in neuronal differentiation of embryonic stem cells and DA precursors, and was a logical pathway to examine. Our data indicates that NT2N neurons, differentiated in NT2 spheres, express a stable dopaminergic phenotype without the use of retinoic acid. Our data also implicate the involvement of the Wnt signaling pathway, and the role of connexin 43 in the differentiation of NT2 cells to NT2N neurons within NT2 spheres.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
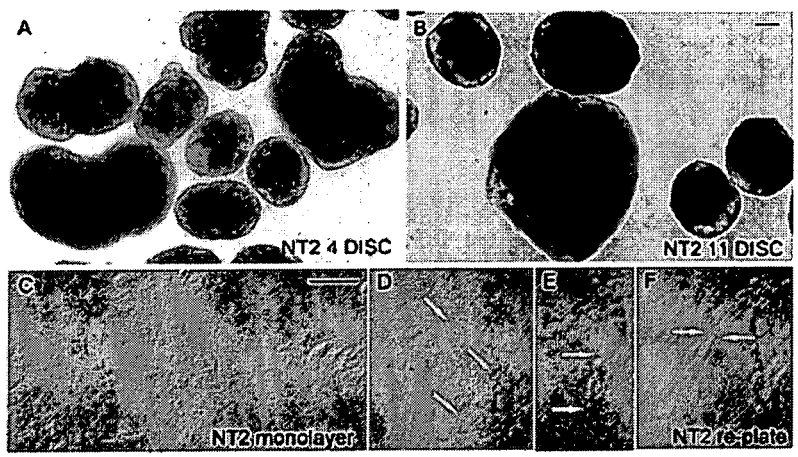
FIG. 1 is a photomicrograph of (C) NT2 cells grown in conventional culture as a monolayer compared to (A) NT2 cells grown for 4 days in suspension culture (DISC), (B) and for 11 DISC. Cells in conventional culture spread and form a confluent monolayer. However, NT2 cells adhere to each other and form spheres in 3-dimensional suspension culture. After 4 DIV in suspension culture, all NT2 cells were aggregated as NT2 spheres. The NT2 spheres remain intact and continue to grow after 11 DIV in suspension culture. (D-F) NT2 11 DISC were re-plated for an additional 11 days.
Figure 2:
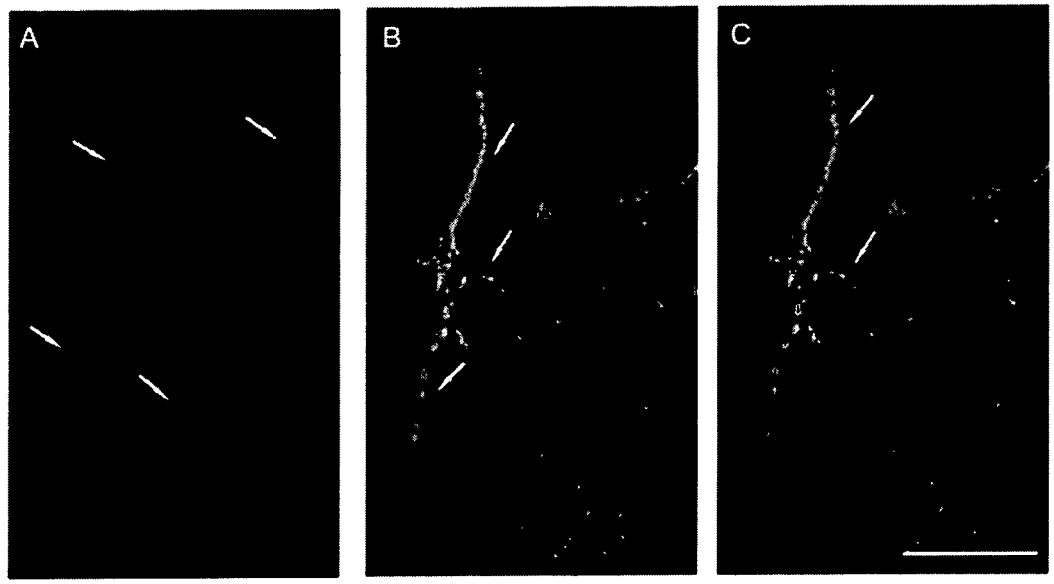
FIG. 2 is a fluorescent photomicrograph of NT2 spheres. (A) 11 DISC NT2 sphere after re-plate for an additional 11 days show TH+ cells (red when viewed in color/lighter region when viewed in greyscale), (B) Neurite outgrowth show immunoreactivity to synaptophysin (green when viewed in color/lighter region when viewed in greyscale). (C) Double label of TH+ cells showing long, extend synaptophysin+ neurite outgrowth.
Figure 3:
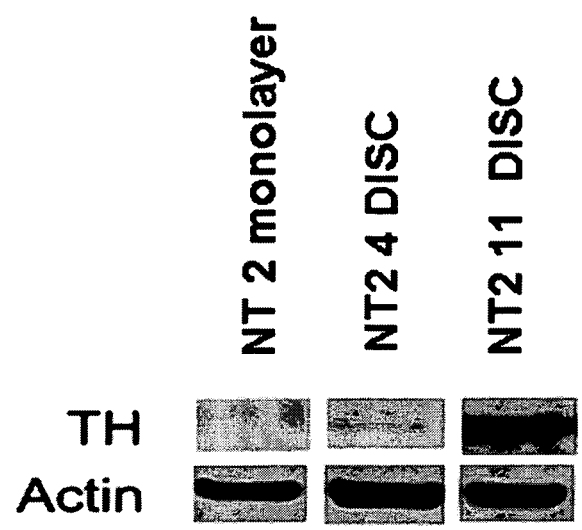
FIG. 3 shows a western blot analysis showing increased TH expression in NT2 spheres after 11 DISC.
Figure 4:
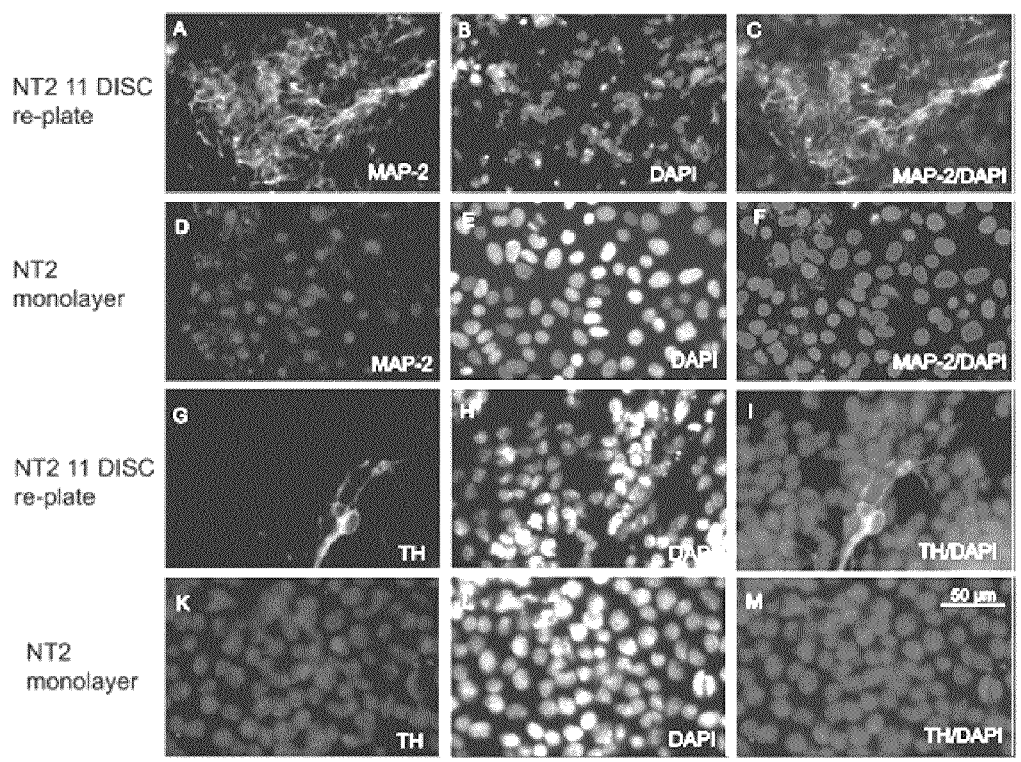
FIG. 4 is a fluorescent photomicrograph of NT2 cells grown in conventional culture compared to NT2 spheres grown in 3-dimensional suspension culture. (A-F) Immunohistochemistry was done to detect Map-2 in these two culture conditions. There was an increase in Map-2+ cells in NT2 spheres, but not in NT2 cells in conventional culture. (G-M) Immunohistochemistry was done to detect TH in these two culture conditions. There was an increase in TH+ cells in NT2 spheres with TH+ neurite outgrowth, but not in NT2 cells in conventional culture. Scale bare=50 μm.

A method of differentiating adult stem cells, such as the teratocarcinoma cell line Ntera2/D1 clone (NT2) available from ATCC, has been developed. The method differentiates the NT2 cells to neurons with a stable neurotransmitter phenotype without the use of growth factors or retinoic acid. The growth factors and/or retinoic acid can be difficult to completely remove during commercial production, highlighting the importance of developing methods not requiring their use. Specific neurotransmitters were identified in these differentiated NT2-derived neurons (NT2-N) after 30 days in culture or 30 days survival in vivo.

The effect of 3-dimensional cell aggregation suspension culture on neuronal differentiation of the embryonal teratocarcinoma cell line NT2 cells without RA treatment is a fundamental aspect of the present invention. The first description of NT2 cell aggregation [Cheung W M, W Y Fu, W S Hui and N Y Ip. (1999)] showed that the aggregation technique shortened NT2 differentiation time from 5 to 3 weeks of RA treatment. More recent studies documented that the aggregation techniques allowed for decreased RA treatment, usually deemed essential for neuronal differentiation of NT2 cells. Megiorni and colleagues reported the presence of mRNA and protein of multiple neuronal markers during RA differentiation of NT2 floating aggregates [Megiorni F, B Mora, P Indovina and M C Mazzilli. (2005)]. Another study by Paquet-Durand and colleagues led those to posit that both RA and cell aggregation have a synergistic role in NT2 cell differentiation [Paquet-Durand F, S Tan and G Bicker. (2003)]. However, those authors did not conclude that cell aggregation alone is not sufficient to induce neuronal differentiation.

In the present study we show, for the first time, that teratocacinoma derived NT2 cells can differentiate to a dopaminergic phenotype by aggregation in a 3-dimensional suspension culture and re-plate without RA treatment. As described by Cheung, NT2 cell aggregation without RA was sufficient to induce low levels of phosphorylated neurofilament protein [Cheung W M, W Y Fu, W S Hui and NY Ip. (1999)]. Cell aggregation for at least 12 days with exposure to 0.1 μm RA for a brief period, followed by re-plating, was essential to induce differentiation of these cells to an observable neuronal phenotype. In our culture conditions, prolonged re-plating period of the NT2 spheres up to 11 days appears to be one factor contributing to the neuronal characteristics of the re-plated NT2 spheres that we observe. The advantage of the dopaminergic phenotype acquired by NT2N through aggregation in a 3-dimensional suspension culture alone over that induced by RA, which results in the loss of the dopminergic phenotype of NT2N within one week [Saporta S, C V Borlongan and P R Sanberg. (1999); Willing A E, T Zigova, M Milliken, S Poulos, S Saporta, M McGrogan, G Snable and P R Sanberg. (2002); Baker K A and I Mendez. (2005)], is that aggregation leads to a stable dopaminergic phenotype for at least 14 days in vitro.

In addition, we also show that the non-RA differentiated NT2N in the re-plated NT2 spheres express neuronal markers such as MAP-2 and synaptophysin. These data indicate that NT2N differentiated by aggregation and then re-plated show characteristics of mature neurons. The presence of synaptophysin, a protein present in pre-synaptic terminals, also suggests that aggregation/re-plate differentiated NT2N have functional synapses [Wiedenmann B and W W Franke. (1985)]. A previous study demonstrated that NT2N neurons form functional excitatory glutamatergic and inhibitory GABAergic synapse when co-cultured with primary astrocytes [Hartley R S, M Margulis, P S Fishman, V M Lee and C M Tang. (1999)]. Our finding also supports a recent study that showed significant transcriptional up-regulation of synapsin I, II and III in RA differentiated NT2 re-plated spheres [Leypoldt F, M Flajolet and A Methner. (2002)].

Signaling Pathway (s) Involved in NT2 Sphere Differentiation:

Differentiation of neuronal precursors has been widely sought, and RA participates in the normal differentiation of neurons during development [Bibel M, J Richter, K Schrenk, K L Tucker, V Staiger, M Korte, M Goetz and Y A Barde. (2004)]. However, a three dimensional environment also stimulates differentiation in vivo [Layer PG, A Robitzki, A Rothermel and E Willbold. (2002)] and cell fate specification [Hamazaki T, M Oka, S Yamanaka and N Terada. (2004)], as it allows tissue-like cell arrangements and cell-to-cell contact. Cellular interaction among adjacent cells is considered a key factor in initiation of signal transduction that guides differentiation. For example, it was shown that oligodendrocyte-neuronal contact activates the PKC pathway, which is involved in cell proliferation, differentiation, and apoptosis in oligodendrocytes [He M, D G Howe and K D McCarthy. (1996)]. Furthermore, transfection of embryonic carcinoma P19 cells with Sox 6 led to enhanced neuronal differentiation through activation of Wnt-1, Mash-1, N-cadherin, E-cadherin and Map-2 genes expression [Hamada-Kanazawa M, K Ishikawa, K Nomoto, T Uozumi, Y Kawai, M Narahara and M Miyake. (2004)]: up-regulated Wnt-1 and Mash-1 resulted in neurogenesis, while aggregation and cell-to-cell interaction induced E-cadherin and N-cadherin, enhancing neuronal differentiation.

Figure 21:
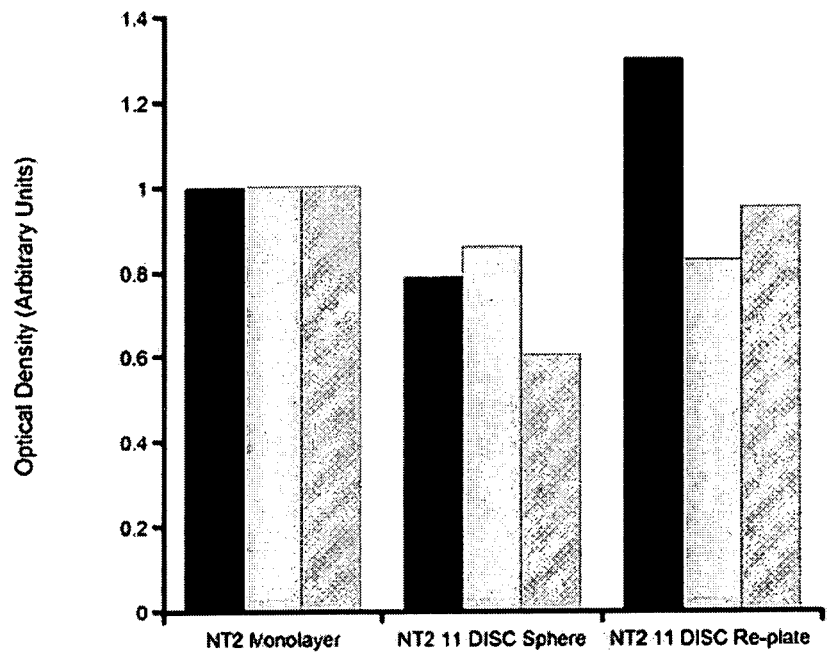
FIG. 21 is a graph illustrating β-catenin/GSK-3β expression in 11 DISC NT2 spheres and 11 DISC re-plate together with undifferentiated NT2 cells in monolayer by western blot analysis. There was 1.2 fold decrease in the cytoplasmic β-catenin in both 11 DISC NT2 spheres and 11 DISC NT2 re-plate compared to undifferentiated NT2 monolayer. Nuclear β-catenin showed 1.2 fold decrease in the 11 DISC NT2 spheres; however in the 11 DISC NT2 re-plate there was 1.3 fold increase in the nuclear β-catenin. There was almost no change in the inactive phosphorylated GSK-3β in 11 DISC NT2 re-plate while NT2 11 DISC spheres had a 1.6 fold decrease in the phospho-GSK-3β. Actin was used as a loading control.

The present methodology shows that aggregation plays a pivotal role in differentiation of NT2 cells. In the NT2 sphere model, there was down-regulation of unphosphorylated cytoplasmic β-catenin in both NT2 11 DISC spheres and the re-plated NT2 11 DISC spheres (FIG. 21). However, nuclear β-catenin was markedly up-regulated in the re-plated NT2 11 DISC spheres indicating nuclear translocation of β-catenin where it may activate β-catenin induced transcription. Additionally, phosphorylated cytoplasmic GSK-3β, which is responsible for phosphorylation and degradation of β-catenin, was down-regulated in the NT2 11 DISC spheres, while it is found in near-normal levels in the re-plated NT2 11 DISC spheres. This finding is consistent with the subsequent increase in nuclear β-catenin seen in re-plated NT2 11 DISC spheres. Additionally, β-catenin is one of the cytoplasmic components of the Wnt pathway, which also has been shown to play a role in neuronal differentiation of embryonic stem cells and DA precursors [Otero J J, W Fu, L Kan, A E Cuadra and J A Kessler. (2004); Castelo-Branco G, N Rawal and E Arenas. (2004)]. In this NT2 re-plated sphere model the stabilization and translocation of β-catenin to the nucleus, likely leads to TCF/LEF transcription activity [Castelo-Branco G, N Rawal and E Arenas. (2004); Kikuchi A. (2000); Grimes C A and R S Jope. (2001); Katoh M. (2002); Jope R S and G V Johnson. (2004)]. Activation and stabilization of β-catenin may be occurring through participation of the Wnt differentiation pathway resulting in down-regulated GSK-3β, and stabilization and translocation of β-catenin to the nucleus, where it targets TCF/LEF transcription [Otero J J, W Fu, L Kan, A E Cuadra and J A Kessler. (2004); Willert J, M Epping, J R Pollack, P O Brown and R Nusse. (2002)]. However, other pathways may be involved, as well, such as the phosphoinositol 3-kinase protein kinase B (PI3K/Akt), protein kinase A (PKA), or protein kinase C (PKC) cell signaling pathways acting through regulation of GSK-3 [Jope R S and G V Johnson. (2004)].

Transcription Activation in the NT2 Spheres:

Induction of dopamine neurons in the midbrain is determined by a combination of many factors during development. The first up-regulated genes in the mesencephalon include Engrailed ½ (En½), Pax⅖, Wnt1 and Lmx1b in a closely regulated sequence [Smidt M P, S M Smits and J P Burbach. (2003)]. Nurr1 transcription factor is expressed just prior to TH expression, which also requires co-expression of Pitx3 [Smidt M P, S M Smits and JP Burbach. (2003); Riddle R and JD Pollock. (2003)]. Lmx1b is expressed in early development of mesencephalic dopamine neurons, promoting their proliferation and survival. Lmx1b is expressed in all mesencephalic dopamine neurons prior to Nurr1 expression [Riddle R and JD Pollock. (2003)]. Smidt and colleagues proposed that transcription activity in mesencephalic dopamine neurons can be summarized in 3 gene pathways: the dopamine synthesis pathway that requires Nurr1 expression, the Lmx1b and Pitx3 pathways that maintain the dopaminergic phenotype over time, and the En½ survival pathway [Smidt M P, S M Smits and J P Burbach. (2003); Simon H H, L Bhatt, D Gherbassi, P Sgado and L Alberi. (2003)] that is essential for the survival of dopaminergic neurons. In this study we have shown that Lmx1b, a factor that is expressed in mesencephalic dopamine neurons, is up-regulated in 11 DISC spheres and 11 DISC re-plated spheres, as is Pitx3 and TH. Importantly, Nurr1 is also up-regulated in both differentiated 11 DISC spheres and re-plated spheres, consistent with their differentiating to a dopaminergic neural phenotype. However, undifferentiated NT2 cells also express Nurr1 [Misiuta I E, L Anderson, M P McGrogan, P R Sanberg, A E Willing and T Zigova (2003)]. This suggests that undifferentiated NT2 cells are similar to dopaminergic precursors capable, under the proper circumstances, to become a dopamine-like neuron. Aggregation of these cells to form spheres, and re-plating the spheres allowing cells to re-adhere to a substrate, enhances their dopaminergic differentiation. Re-adhered cells from NT2 spheres express all essential mesencephalic dopaminergic transcription factors.

Previous work has shown that Wnt 1 and Wnt 5a increase the number of dopaminergic neurons in Nurr1+ precursors [Castelo-Branco G, J Wagner, F J Rodriguez, J Kele, K Sousa, N Rawal, H A Pasolli, E Fuchs, J Kitajewski and E Arenas. (2003)], which may lead to activation of the Wnt/β-catenin pathway. However, another study suggested that up regulated Nurr1 expression is a consequence of activation of the PKA and/or PKC pathway [Satoh J and Y Kuroda. (2002)].

Tumor Formation and NT2 Spheres:

One impetus of the present invention was the development an improved cell source for transplantation in Parkinson's disease. Parkinson's disease (PD) is a neurodegenerative disease characterized by loss of the dopaminergic neurons in the substantia nigra pars compacta. Patients with PD present with tremor, bradykinesia, and rigidity, as well as cognitive disorders. Treatment with L-dopa to restore dopamine in the striatum is the primary pharmacological treatment, and is initially effective, though patients usually develop tolerance after long-term treatment. Therefore, the use of cell replacement therapy for PD has been considered a hopeful long-term treatment goal. Cell transplantation therapy using fetal dopaminergic neurons into the striatum ameliorates behavioral deficits in animal models of PD [Bjorklund A and O Lindvall. (2000)]. However, ethical concerns limit the use of human embryonic stem cells and fetal neural cells for transplantation. Human, double blind, placebo controlled, clinical trials that transplanted fetal dopaminergic neurons in PD patients reported controversial results. A trial to compare transplantation efficacy in younger and older patients showed that patients' pre-operative response to L-dopa, not the patients' age, predicted improvement of UPDRS motor "off" scores [Freed C R, M A Leehey, M Zawada, K Bjugstad, L Thompson and RE Breeze (2003)]. Additionally, some patients developed dyskinesia after one or two years of clinical improvement. Another clinical trial also reported mixed results with no overall clinical improvements, as more than 50% of patients develop off medication biphasic dyskinesia [Olanow C W, C G Goetz, J H Kordower, A J Stoessl, V Sossi, M F Brin, K M Shannon, G M Nauert, D P Perl, J Godbold and T B Freeman. (2003)]. However, these authors conclude that their patients' dyskinesia was likely the result of patchy release of dopamine provided by the transplant. Thus, the outcome from such clinical trials is not yet optimal due to technical issues concerning the transplantation procedure and tissue preparation. In order for a successful cell therapy procedure to be established, dopaminergic neurons of uniform quality that can be obtained in large numbers and that are free of biohazards must be used to achieve consistent results [Redmond D E, Jr. (2002)].

In view of the fact that NT2 spheres are derived from an embryonal teratocarcinoma, there is a possibility of tumor formation post-transplantation. Nevertheless, the possibility of tumor formation by transplanted undifferentiated NT2 cells that are still dividing must be ruled out. The nuclear protein Ki-67 is expressed in all proliferating cells [Gerdes J, H Lemke, H Baisch, H H Wacker, U Schwab and H Stein. (1984)]. Those cells that do not express K167 are in Go and have exited the cell cycle. Our results show that Ki-67 is markedly down-regulated in the re-plated NT2 11 DISC spheres compared to NT2 monolayer. Withdrawal from the cell cycle is necessary for terminal differentiation, and we suggest that growth arrest of the re-plated NT2 spheres may be a consequence of NT2N neuron differentiation within the NT2 spheres compared to the undifferentiated NT2 monolayer. A previous in vivo study discussed this issue, stating that NT2 cells form lethal tumors when transplanted in peripheral organs or most parts of the central nervous system. However, when transplanted in the caudate-putamen complex of nude mice, NT2 cells showed engraftment for 33 weeks post-transplantation with no tendency to form tumors [Miyazono M, P C Nowell, J L Finan, V M Lee and J Q Trojanowski. (1996)]. A more recent study by Ferrari and colleagues contradict the former study. They showed that intracortical transplantation of undifferentiated NT2 cells survive, migrate and differentiate into neuron and glia like cells in P0 normal mice with no tendency of tumor formation after 3 weeks post transplant [Ferrari A, E Ehler, R M Nitsch and J. Gotz. (2000)]. We propose that aggregation of NT2 cells in 3-dimensional suspension culture is sufficient to induce neuronal differentiation. Additionally, aggregation is able to generate a more stable dopaminergic phenotype than differentiation of NT2 with RA.

The invention is described below in examples which are intended to further describe the invention without limitation to its scope.

Example 1

Figure 5:
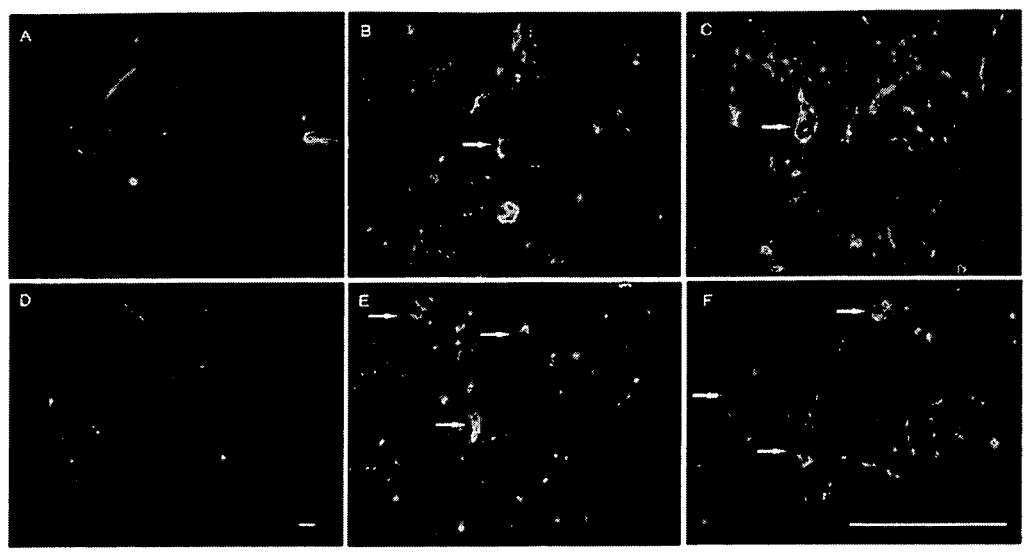
FIG. 5 is a fluorescent photomicrograph of NT2 spheres one month post-transplantation in the host striatum. (A) and (D) NT2 spheres engraft in the host striatum. (B) and (C) TH+ cells (white arrows) one month post-transplant. (E) double label of TH+ cells (green when viewed in color) and human mitochondria (red when viewed in color). (F) double label of TH+ cells (green when viewed in color) and human nuclei (red when viewed in color). Scale bar=100 μm.
Figure 6:
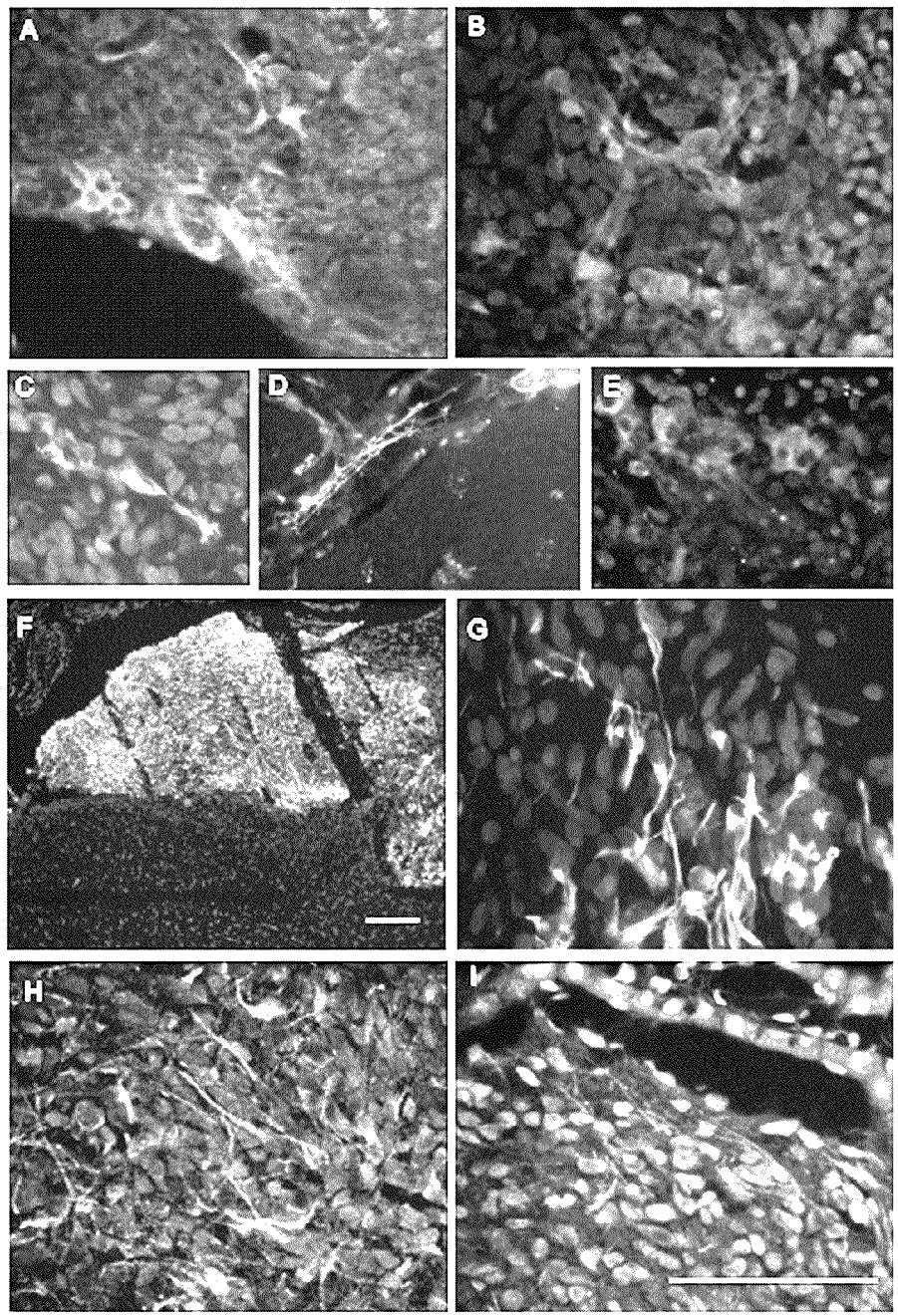
FIG. 6 is a fluorescent photomicrograph of NT2 spheres one month post-transplantation in the host striatum. (A) to (E) TH+ cells (red when viewed in color) in the host striatum one month post-transplant. (C) and (D) extensive TH+ neurite outgrowth within the transplant site. (F) and (G) nestin+cells (red when viewed in color) within the graft. (H) and (I) NF+neurites (red when viewed in color) extend from the graft to host striatum. Scale bar=100 μm.
Figure 7:
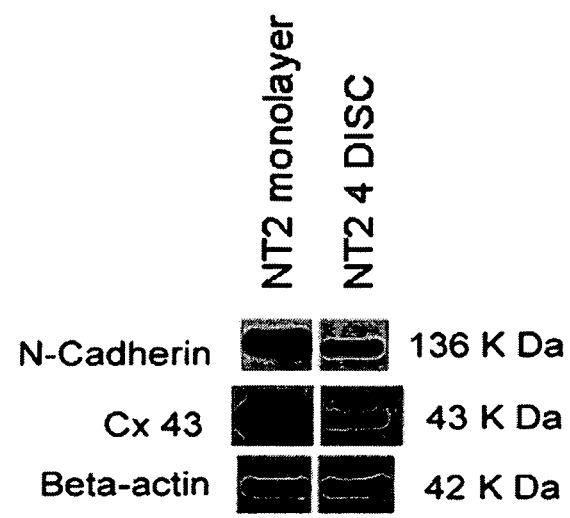
FIG. 7 shows a western blot analysis demonstrating decreased expression of the cell adhesion molecule N-cadherin and gap junction protein connexin Cx43 in NT2 4 DISC spheres compared to NT2 monolayer cell culture. The decrease of Cx43 expression is consistent with differentiation of NT2cells in NT2 spheres.
Figure 8:
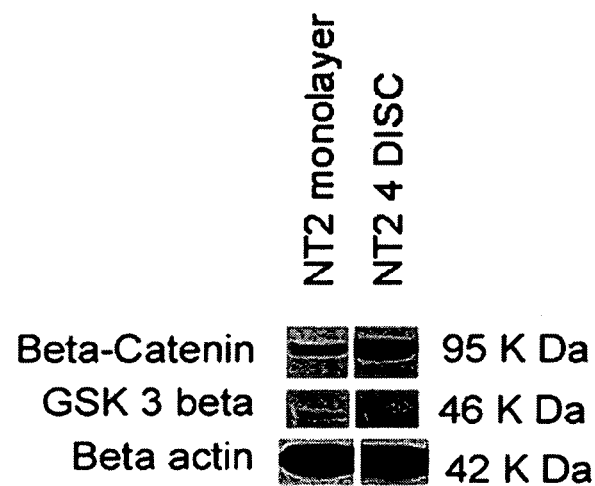
FIG. 8 shows a western blot analysis demonstrating an increase in unphosphorylated β-catenin expression in NT2 4 DISC spheres compared to NT2 monolayer, with almost no change in GSK-3β. These findings suggest the stabilization of β-catenin within the cytosol, and possible translocation to the nucleus.
Figure 9:
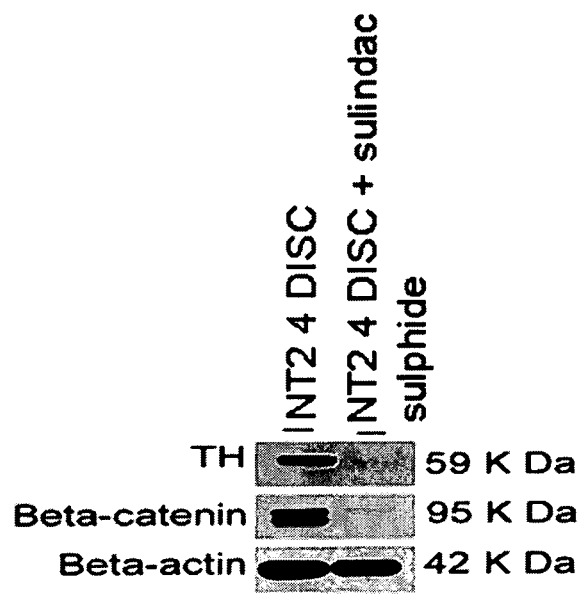
FIG. 9 shows a western blot analysis demonstrating a decrease in TH expression in NT2 4 DISC spheres treated with sulindac sulphide, a β-catenin inhibitor, suggesting the possible involvement of the Wnt/β-catenin pathway in the differentiation of NT2 cells in NT2 spheres.
Figure 10:
FIG. 10 shows RT-PCR analysis of NT2 cells in monolayer, 4, 11 and 14 DISC NT2 spheres. There was up regulation in LEF-1 mRNA in 4 DISC (1.1 fold), 11 DISC (1.8 fold) and 14 DISC (3.1 fold) in NT2 spheres. The up regulation in LEF-1 mRNA was associated with up regulation of TH mRNA in 4 DISC (4.5 fold), 11 DISC (11.7 fold) and 14 DISC (14.4 fold) NT2 spheres. Nurr 1 was expressed in undifferentiated NT2 monolayer and NT2 spheres. GAPDH amplification was used as control.
Figure 11:
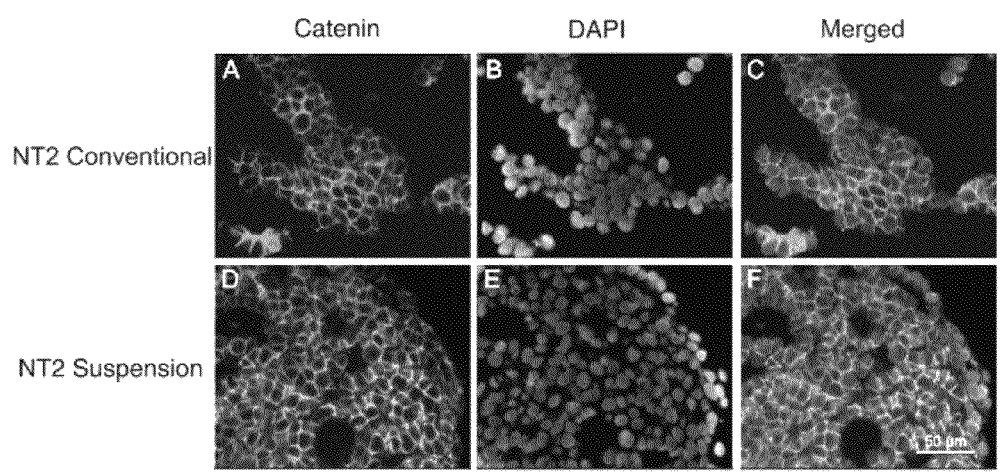
FIG. 11 is a series of fluorescent photomicrographs showing marked increase of β-catenin in NT2 spheres grown in 3-dimensional suspension culture compared to NT2 monolayer cell culture. The increase in the unphosphorylated (active) form of β-catenin in the cytosol with a slight increase in the nucleus suggests the involvement of the Wnt/β-catenin pathway in the differentiation of NT2 cells in NT2 spheres.
Figure 12:
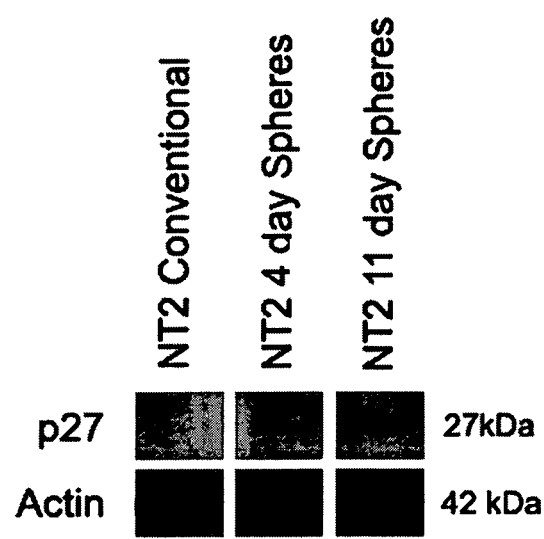
FIG. 12 shows a western blot analysis showing an increase in p27 expression in NT2 spheres after 4 and 11 DISC compared to monolayer culture, indicating withdrawal of cells in NT2 spheres from the cell cycle.
Figure 13:
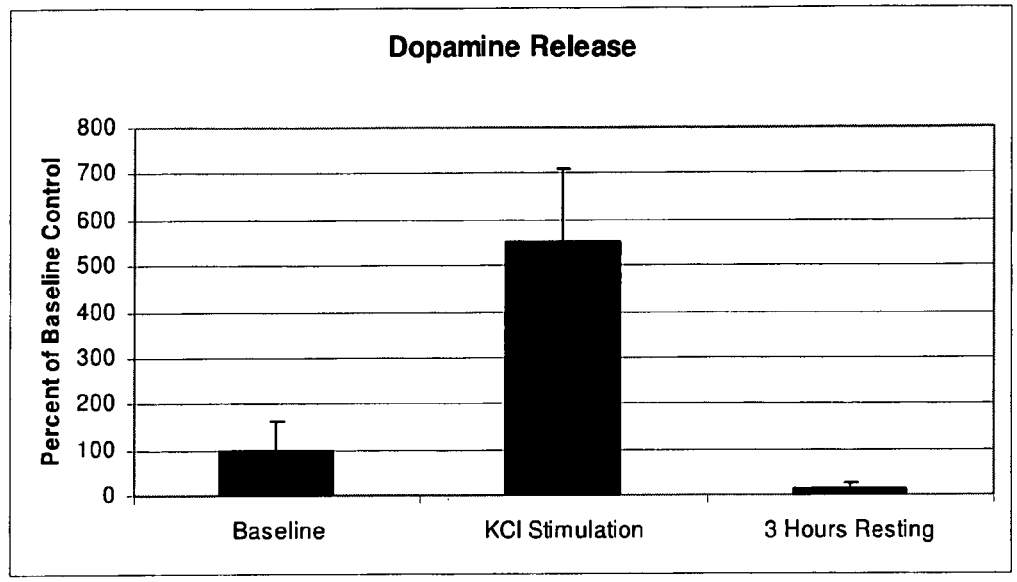
FIG. 13 is a graph illustrating dopamine release. HPLC analysis of DA concentrations in media collected from NT2 11 day spheres replated 14 days on PLL reported as percentage of baseline control. Baseline, unstimulated cell media (n=8) and media collected from replated spheres allowed to rest for 3 hours after KCl stimulation (n=8) had mean concentrations of 0.2375 nM and 0.03 nM, respectively. Media collected from replated NT2 spheres stimulated with KCl for 20 minutes (n=8) had a mean DA concentration of 1.20875 nM, a 6-fold increase from baseline (p<0.05).
Figure 14:
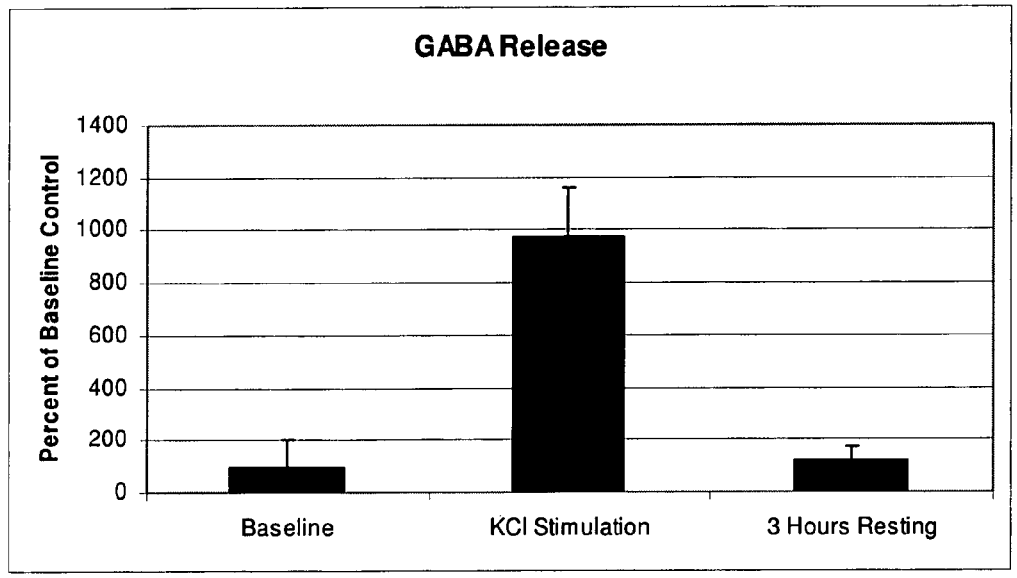
FIG. 14 is a graph illustrating GABA release. CZE-LIF analysis of GABA concentrations in media collected from NT2 11 day spheres replated 14 days on PLL reported as percentage of baseline control. Baseline, unstimulated cell media (n=8) and media collected from replated spheres allowed to rest for 3 hours after KCl stimulation (n=8) had mean concentrations of 0.7625 nM and 0.9375 nM, respectively. Media collected from replated NT2 spheres stimulated with KCl for 20 minutes (n=8) had a mean GABA concentration of 7.4375 nM, a 10-fold increase from baseline (p<0.05).
Figure 15:
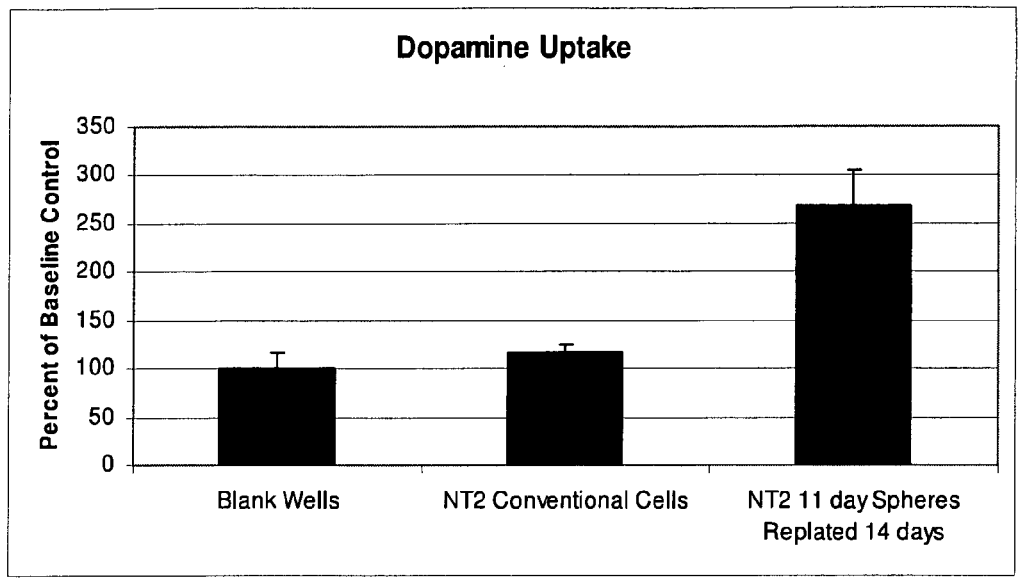
FIG. 15 is a graph illustrating dopamine uptake. Cellular uptake of 3H-DA in blank wells, NT2 conventional cells, and NT2 11 day spheres replated 14 days on PLL was analyzed using liquid scintillation spectrometry and is reported as percentage of blank control. Blank wells (n=3) had a mean radioactivity level of 103.2 count per million (CPM). NT2 conventional cells did not take up significantly more 3H-DA than blank wells (n=8, M=120.1 CPM, p>0.05). NT2N neurons in replated NT2 spheres had a mean radioactivity level of 276.09 CPM, a significant increase from blank wells and NT2 conventional cells (p<0.05).
Figure 16:
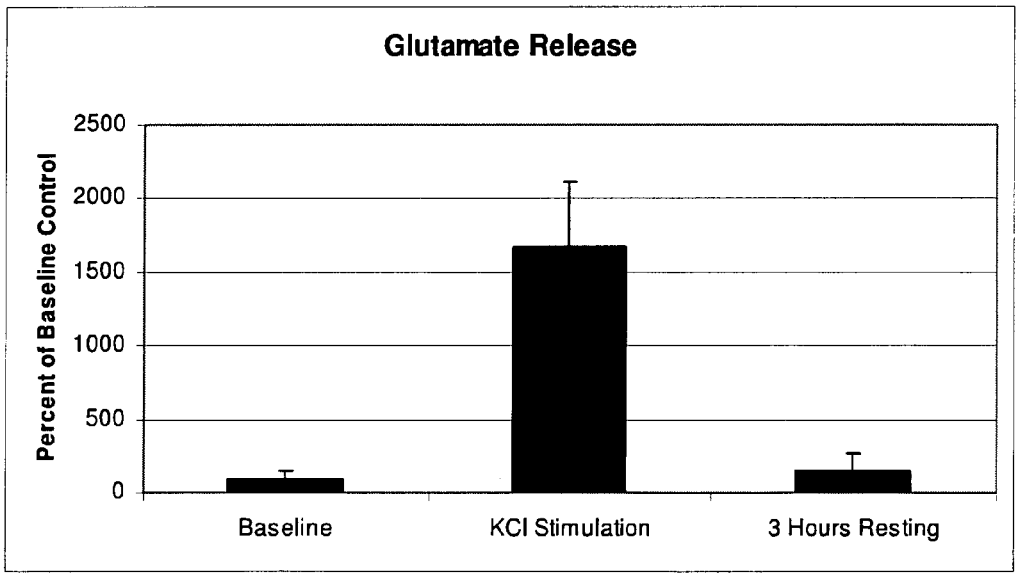
FIG. 16 is a graph illustrating glutamate release. CZE-LIF analysis of glutamate concentrations in media collected from NT2 11 day spheres replated 14 days on PLL reported as percentage of baseline control. Baseline, unstimulated cell media (n=8) and media collected from replated spheres allowed to rest for 3 hours after KCl stimulation (n=8) had mean concentrations of 0.10222 mM and 0.15 mM, respectively. Media collected from replated NT2 spheres stimulated with KCl for 20 minutes (n=8) had a mean glutamate concentration of 1.71444 mM, a 17-fold increase from baseline (p<0.05).

Differentiated NT2N Neurons Derived from Aggregated NT2 Cells not Exposed to Retinoic Acid Survive and Engraft in the Rat Striatum Results FIGS. 1 through 4 show that NT2 spheres differentiate to dopaminergic neurons without retinoic acid. FIGS. 5 and 6 show that NT2 spheres survive in the host striatum and retain their dopaminergic phenotype. FIGS. 7 through 11 show possible signaling pathways for NT2 differentiation. The results demonstrate that there is an increase in the expression of TH in NT2N neurons within NT2 spheres grown in 3-dimensional suspension culture after 4 DISC without retinoic acid treatment, compared to NT2 cells grown in monolayer conventional culture. TH expression is markedly increased in re-plated 11 DISC NT2 spheres together with expression of multiple neuronal markers such as MAP-2 and synaptophysin. There is also increased unphosphorylated β-catenin in NT2 spheres, with almost no change in GSK-3β, and a marked decrease in N-cadherin, compared to NT2 cells grown in conventional culture. These findings implicate the involvement of the Wnt signaling pathway in neuronal differentiation of cells in NT2 spheres.

Additionally, the non-steroidal anti-inflammatory sulinac sulfide, a β-catenin inhibitor, decreased TH expression, further suggests the involvement of the Wnt signaling pathway. Therefore, differentiation of NT2 cells within NT2 spheres to dopaminergic NT2N neurons is dependent, at least in part, on the Wnt signaling pathway.

Transcription analysis using RT-PCR showed up-regulation of LEF-1 overtime, which coincides with up-regulated TH transcription, further implicates activation of the Wnt pathway.

Nurr-1 transcription is present in both NT2 cells and in NT2 spheres. NT2 spheres survive in the host striatum, and retain their dopaminergic phenotype, as they continue to express TH and other neuronal markers in vivo for one month post-transplant.

Materials And Methods

NTera2/D1 cells:

The NTera2/D1 (NT2; ATCC) were thawed quickly at 37° C. until just before the last ice crystals were gone. The cells were gently transferred to a 15 cc centrifuge tube filled with 10 ml of DMEM:F12 and 10% fetal bovine serum (FBS) and 0.1% gentamicin (maintenance medium). The cells were centrifuged at 700 rpm for 7 min, the supernatant discarded, and the cells resuspended in 1 ml of the DMEM:F12/FBS media. Viability and cell number were assessed using the trypan blue dye exclusion method.

Differentiation Protocol (Formation of NT2 Spheres):

The NT2 precursors were thawed at 37° C. (as described above). The cells were gently transferred to a 15 ml centrifuge tube containing 10 ml of Dulbecco's Modified Eagle's Medium (DMEM), 10% fetal bovine serum (FBS), and 0.1% gentamicin (Sigma), centrifuged resuspended in 1 ml of the DMEM/FBS media. NT2 precursors were seeded at $1 \times 10^7$ cells/50 ml in 150 mm plates in the same medium as described and sub cultured when they achieved 70-80% confluency. NT2 cells were seeded at a density of $2 \times 10^6$ cells/ml in ultra low attachment polystyrene 6 well plates (Costar) in DMEM, 10% FBS, 0.1% gentamicin. Media were supplemented daily for the duration of the experiment.

Inhibitors were used through out the experiment. The final concentration was 1 μm for AKT inhibitor (wortmannin, cell signalling) and 100 μm for β-catenin inhibitor (sulindac sulphide, sigma).

Western Blot:

Conventional cultures of NT2 cells and NT2 spheres were prepared by washing them in phosphate buffered saline (PBS), scraping the NT2 cells from the culture dish and placing the harvested cells into cold PBS and stored at −80° C. until they were analyzed. Frozen samples were thawed quickly in lysis buffer and 1 μM dithiothreitol, and sonicated. Protein samples and molecular weight markers (Amersham Bioscience) were resolved on 10% SDS-PAGE gel, and transferred to Invitrolon PVDF membranes (Invitrogen). The membranes were incubated in TBS containing 5% non-fat milk and 0.1% Tween-20 for 1 hour at room temperature to block non-specific binding, and then incubated overnight in appropriate antibody at 4° C. The membranes were washed, in TBS with 0.1% Tween-20, and incubated in peroxidase-conjugated anti-rabbit IgG (1:20,000; Jackson ImmunoResearch) for 1 hour at room temperature. Primary and secondary antibodies were diluted in TBS, 5% non-fat milk and 0.1% Tween-20. Immunoreactivity was visualized using a West Pico Chemiluminescent Kit (Pierce Biotechnology). Digitized images of the films will be analyzed using Image Pro-Plus (Media Cybernetics, Silver Springs, Md.) software.

Antibodies for Western Blot:

Tyrosine hydroxylase (TH) 1:500, (Pelfreeze), β-actin 1:10000, (Sigma), phosphorylated AKT 1:500, (Cell Signaling Technology), N-cadherin 1:1000 (Zymed Laboratories), Cx43 1:1000, (Zymed Laboratories), β-catenin 1:5000, (BD Biosciences), Glycogen synthase kinase 3β (GSK-3β) 1:1000, (Calbiochem), TAU1:1000 (Sigma), P27 1:500 (Calbiochem), Neuro D1 1:1000 (Chemicon).

Immunohistochemistry:

NT2 cells and NT2 spheres were removed with their culture medium from plates and centrifuged for 5 min at 700 rpm. The pellet were briefly rinsed in cold PBS, recentrifuged and immersed fixed for 1 hr in 4% paraformaldehyde prepared in PBS. The NT2 cells and NT2 spheres were washed in PBS, embedded in HistoGel (Richard-Allen Scientific), dehydrated through an ascending ethanol series, cleared in xylene and embedded in paraffin blocks. Sections were incubated overnight at 4° C. in the appropriate antibody. The following day, sections were washed 3 times and incubated with goat anti-mouse Alexa 488 (Molecular probes) 1:200 for 1 hr at room temperature, or goat anti-rabbit conjugated to Alexa 594 dye. Slides were washed 3 times, coverslipped with Vectashield with DAPI (Vector Laboratories Inc.)

Antibodies for Immunohistochemistry:

Tyrosine hydroxylase (TH) 1:400, (Pel Freeze), Nestin 1:500, (Chemicon), Neuofilament 1:200 (Zymed), Human mitochondria 1:20 (Chemicon), Human nuclei 1:20 (Chemicon), Map-2 1:500 (Chemicon), synaptophysin 1:1500 (Chemicon).

RT-PCR:

Total RNA was isolated from NT2 cells grown in conventional culture and 4, 11, and 14 DISC NT2 spheres using TRI Reagent (Sigma) followed by cDNA synthesis from 5 μg of total RNA using SuperScript First strand synthesis (Invitrogen). The following PCR conditions were optimized as shown: GAPDH (5' accacagtccatgccatcac 3', 5' tccaccaccct-gttgctgta 3', 30 cycles, 60° C.), TH (5' tgtcagagctggacaagtgt 3', 5' gatattgtcttcccggtagc 3', 33 cycles, 58° C.), LEF-1 (5' ctaccacgacaaggccagag 3', 5' cagtgaggatgggtagggttg 3', 30 cycles, 62° C.) and Nurr 1 (5' ttctcctttaagcaatcgccc 3', 5' aagcctttgcagccctcacag 3', 35 cycles, 60° C.). Digitized images of the films were analyzed using Image Pro-Plus (Media Cybernetics, Silver Springs, Md.) software. The level of mRNA was estimated by measuring the optical density of mRNA bands using Image Pro-Plus (Media Cybernetics) as mentioned above.

Transplantation:

Rats were anesthetized with Ketamine (0.35 ml/KG) and maintained with Flurothane gaseous anesthesia. Animals were placed in a stereotaxic frame, and bregma located through an incision at the vertex of the head. NT2 spheres were withdrawn up in a 10 μl microsyringe fitted with a 26 g thin-wall needle (200 μm internal diameter) and approximately 200,000 cells were deposited in the striatum. NT2 spheres were collected as described for western blot analysis, but washed in Hanks' balanced salt solution. Medium injection consisted of 2 μl of Hanks' balanced salt solution. The coordinates for the injections were 1.2 mm anterior to bregma, 2.7 mm laterally and 5 mm ventral to dura, with the toothbar set at zero. Each injection were delivered at a rate of 1 μl/min. The needle was held in place for an additional 5 minutes after the completion of the injection before being slowly withdrawn. The incision was sutured with wound clips.

Preparation of Brain Containing Transplanted SC-NT2 Tissue Constructs and NT2 Spheres:

Rats, deeply anesthetized with sodium pentobarbital (60 mg/Kg), were transcardially perfused with normal saline followed by 4% paraformaldehyde in 0.1 M phosphate buffer and the brain removed. Brains were post-fixed for 12 hours in 4% paraformaldehyde, dehydrated through an ascending series of alcohols, cleared in xylene and embedded in paraffin. Sections were cut at 5-7 μm. Every 20th section through the area of the transplant will be stained with cresyl violet to identify the location of the graft.

Example 2

Human NT2-N Neurons Differentiated by the Cell Aggregation Method have Functional Neurotransmitter Systems In Vitro The NTera2/cloneD1 (NT2) human teratocarcinoma cell line is capable of terminal differentiation into postmitotic neurons (NT2N) upon exposure to retinoic acid (RA). These NT2N differentiated with RA (hNT) are a heterogeneous population of neurons expressing multiple neurotransmitter enzymes. hNT neurons harvested and analyzed with High Performance Liquid Chromatography (HPLC) have low but detectable levels of dopamine (DA) present, while NT2 cells do not. Further supporting the in vitro functionality of these neurons, excitatory glutamatergic and inhibitory gamma-aminobutyric acidergic (GABAergic) are formed when hNT neurons are plated on primary astrocytes. However, hNT neurons lose expression of neurotransmitter enzymes after 30 days in vitro and in vivo, indicating loss of phenotype and a probable loss of functionality.

We have developed an alternate method of differentiation using cell aggregation and subsequent substrate contact without the use of RA or exogenous growth factors. NT2 spheres contain immature neurons (NT2-N) after 4 days in suspension culture, and rapidly mature with substrate contact. These NT2-N neurons display stable neuronal phenotypes after 30 days in vitro and in vivo, unlike NT2N (hNT) differentiated using RA. Neurons expressing stable phenotypes may be considered differentiated, though not necessarily fully functional. Mature neurons in vivo are able to both release and take up neurotransmitter. The functional maturity of these neurons in vitro is assessed by examining neurotransmitter release and uptake.

Cultures were stimulated with potassium chloride and analyzed using HPLC with electrochemical detection and Capillary Zone Electrophoresis with Laser Induced Fluorescence (CZE-LIF). Levels of DA, GABA, and glutamate release were examined in NT2-N from replated NT2 spheres. Cellular uptake of 3H-DA was also examined in these cultures. Levels of 3H-DA uptake were measured by liquid scintillation spectrometry in NT2-N from replated NT2 spheres and NT2 cells grown in conventional culture.

Significantly higher levels of DA, GABA, and glutamate were found in medium collected from potassium stimulated NT2-N than unstimulated cells or cells allowed to rest for 3 hours after stimulation. In addition, significantly more radioactive DA was taken into NT2-N than NT2 conventional cultures or blank wells. NT2-N induced by cell aggregation and matured with substrate contact are able to both release and take up neurotransmitters, suggesting that these NT2-N are terminally differentiated, functional neurons after one month in vitro.

FIGS. 1-4 illustrate the results of the experiments. There was shown to be significant increases in media DA, GABA, and glutamate concentrations after KCl stimulation, which indicates that NT2-N neurons found in replated NT2 spheres synthesize and release neurotransmitter after one month in vitro. A high concentration of extracellular potassium causes NT2-N neurons in replated NT2 spheres to release neurotransmitters, which suggests that the membranes of these neurons are polarized and are able to be depolarized after one month in vitro. Since significantly more 3H-DA was found in lysed cells from replated NT2 spheres than NT2 conventional cells, this indicates NT2-N neurons in replated NT2 spheres have functional neurotransmitter uptake systems while NT2 conventional cells do not. NT2-N neurons induced by cell aggregation and matured with substrate contact are able to both release and take up neurotransmitters, which suggests they are functional neurons after one month in vitro.

Materials and Methods

Cell Culture:

The NTera2/D1 cells (NT2; ATCC) were thawed quickly at 37° C. until just before the last ice crystals were gone. The cells were gently transferred to a 15 mL centrifuge tube filled with 10 mL of DMEM with 1% antibiotic/antimycotic (Invitrogen) and 0.1% gentamicin (Sigma) (wash medium). The cells were centrifuged at 800 rpm for 3 min, the supernatant discarded, and the cells resuspended in 1 mL of DMEM:F12 media containing 10% fetal bovine serum (FBS), 1% antibiotic/antimycotic (Invitrogen) and 0.1% gentamicin (Sigma) (maintenance medium). Viability and cell number were assessed using the trypan blue dye exclusion method. NT2 precursors were seeded at 4×106 cells/50 mL in 150 mm plates in the maintenance medium described and sub cultured when they achieved 70-80% confluence. For differentiation, NT2 cells were seeded at a density of 2×106 cells/mL in ultra low attachment polystyrene 6 well plates (Costar) in DMEM:F12 maintenance medium. Media was supplemented daily for the duration of the experiment. After 11 days in suspension culture (DISC), NT2 spheres were collected and replated on 0.01% Poly-L-Lysine (PLL) coated plates. Spheres were split 1:8 onto 24 well plates for cellular uptake studies and 1:16 onto 96 well plates (Nalge Nunc) for HPLC and CZE-LIF studies and grown for 14 days.

High Performance Liquid Chromatography:

50 µl of pre-stimulation media was collected for each sample, then 30 mM KCl was applied for 20 minutes and stimulated cell media was also collected. 5 µl of 0.1M HCl per 50 µl sample was added to avoid further oxidation. Media samples were stored at −80° C. until they were analyzed. A standard curve was generated by adding known quantities of neurotransmitter. Cell culture media without cells was treated in the same manner as sample media. Samples were analyzed using a reverse phase HPLC system (PerkinElmer series 200) coupled to a dual-channel electrochemical detector (model 5100A, ESA, Inc). Detection was performed using a C18 column (4.6 mm×100 mm, 3 µm particles, ODS), and a Chrome Guard pre-column (Varian). The mobile phase was citrate-acetate containing 6.0% methanol and 0.35 mM 1-octane-sulfonic acid, pH 4.0, at a flow rate of 1 mL/minute. Detected peaks were quantified using Total Chrom Workstation software (PerkinElmer) using the standard curve for the neurotransmitter. All results are expressed as mean + or − SEM. Experiments were analyzed using repeated measures analysis of variance and post-hoc analyses were done using a Scheffe post-hoc test.

Capillary Zone Electrophoresis with Laser-Induced Fluorescence:

A capillary electrophoresis system equipped with an argon laser tuned to 488 nm was used (Model R2D2, Meridialysis Co., Merida, Venezuela). A carbonate buffer (20 mM carbonate/bicarbonate) was the running buffer to transport the sample through the capillary when detecting glutamate. Detection of GABA from the samples required a different running buffer consisting of 23 mM borate with 120 mM sodium dodecyl sulfate (SDS) and 1% methanol. The samples or standards were sucked into the anodic end by applying a negative pressure (19 psi or 1.34 kg/cm for 1 s) at the cathodic end of the capillary. Electrophoretic separation was achieved by applying a high voltage between the anode and the cathode for 12 min, 22 kV for glutamate and 26 kV for GABA. Fluorescein isothiocyanate (FITC) was conjugated with glutamate and GABA as the fluorescent chromophore. Optimal concentrations of FITC and the calibration curves for both amino acids have been reported previously. Samples and standards were derivatized with 5 µl of FITC (1 mM) and carbonate buffer (20 mM) mixture. A syringe loaded with FITC-carbonate mixture was placed in a precision pump, and 2 µl of the mixture was delivered into a tube containing sample. The samples reacted overnight (14 hr) at room temperature in a water-saturated chamber that minimizes evaporation. Homoglutamine (10-5 M) was used as an internal standard and was mixed in the carbonate buffer used to derivatize samples and standards. This amino acid was chosen because it is not produced in the mammalian brain. All results are expressed as mean + or − SEM. Experiments were analyzed using repeated measures analysis of variance and post-hoc analyses were done using a Scheffe post-hoc test.

Cellular Uptake of 3H-DA:

Media was removed and the cultures were washed three times with incubation solution (5 mM glucose, 1 mM ascorbic acid in PBS, pH 7.4). Cultures were then preincubated for 5 minutes at 37° C. with 1 mM of incubation solution containing 0.1 mM pargyline (MAO inhibitor). Cells were incubated with 100 nM 3H-Da (37 Ci/mmol) for 15 minutes at 37° C. Blanks were obtained by incubating the cells at 0° C. The uptake was stopped by removing the incubation mixture followed by three rapid washes with PBS. Cells were scraped twice with 1 mL PBS containing 1% triton X-100 and 6% perchloric acid. Radioactivity was measured by liquid scintillation spectrometry after addition of 10 mL of Quantafluor to each vial.

All results are expressed as mean + or − SEM. Experiments were analyzed using one way analysis of variance and post-hoc analyses were done using a Scheffe post-hoc test.

Example 3

Material and Methods for the Examples 4-7

NTera2/D1 cells:

The NTera2/D1 (NT2; ATCC) were thawed quickly at 37° C. until just before the last ice crystals were gone. The cells were gently transferred to a 15 cc centrifuge tube filled with 10 ml of Dulbecco's Modified Eagle's Medium (DMEM:F12), 10% fetal bovine serum (FBS) and 0.1% gentamycin (Sigma). The cells were centrifuged at 700 rpm for 7 min, the supernatant discarded, and the cells re-suspended in 1 ml of the DMEM: F12/FBS media. Viability and cell number were assessed using the trypan blue dye exclusion method.

Formation of NT2 Spheres:

The NT2 cells were gently transferred to a 15 ml centrifuge tube containing 10 ml of DMEM, 10% FBS and 0.1% gentamycin, centrifuged at 700 rpm for 7 min and re-suspended in 1 ml of the DMEM/FBS media. NT2 precursors were seeded at $1 \times 10^7$ cells/50 ml in 150 mm plates in the same medium as described and subcultured when they achieved 70-80% confluence. The cells were lifted using 0.25% trypsin, washed three times in DMEM/FBS and centrifuged at 800 rpm for 5 min. The number of NT2 was determined using a hemocytometer, and viability was assessed using trypan blue dye exclusion.

NT2 cells were seeded at a density of $2 \times 10^6$ cells/ml in ultra low attachment polystyrene 6 well plates (Costar) in DMEM, 10% FBS, and 0.1% gentamycin. Media were supplemented daily for the duration of the experiment. NT2 spheres were either collected at 11 days in suspension culture (11 DISC) or re-plated on poly-L-lysine coated plates for another 11 days (11 DISC re-plated).

Dopaminergic Differentiation of NT2 Cells:

TH is the rate limiting enzyme of dopamine synthesis. The level of TH expression in NT2 spheres and NT2 re-plated was assessed and compared to undifferentiated NT2 cells (NT2 monolayer) using western blot and immunohistochemistry (below). The level of TH mRNA transcription in NT2 spheres and NT2 re-plated was also estimated by RT-PCR and compared to the undifferentiated NT2 cells. Other transcription factors essential for dopaminergic differentiation such as Lmx1B, En-1, Ptx3 and Nurr-1 were also assessed.

β-catenin/GSK-3β Expression:

Activation of β-catenin, the cytoplasmic component of Wnt pathway, was assessed by western blot analysis in NT2 spheres after 11 DISC, NT2 11 DISC re-plated cells and undifferentiated NT2 monolayer. Similarly, levels of cadherin, glycogen synthase kinase 3β (GSK-3β), were determined using western blot analysis (below).

Proliferation of NT2 Cells:

Teratocarcinoma derived undifferentiated NT2 cells proliferate in conventional culture. In order to assess whether NT2 spheres contained proliferating NT2 cells, western blot analysis for the nuclear protein Ki-67, which is present in all cells that have not left the cell cycle [Gerdes J, H Lemke, H Baisch, H H Wacker, U Schwab and H Stein. (1984)], was used to compare continued cell division in undifferentiated NT2 cells with cells in differentiated NT2 spheres.

General Methods

Western Blot:

NT2 monolayer and NT2 11 DISC spheres and re-plated NT2 11 DISC spheres were washed once in phosphate buffered saline (PBS), the NT2 cells scraped from the culture dish and placed the harvested cells into cold PBS. Culture medium in wells containing NT2 spheres was aspirated from the culture wells and centrifuged for 5 min at 700 rpm. The supernatant was discarded and the pellet was re-suspended in cold PBS. All samples were washed once more in PBS and stored at −80° C. until they were analyzed. Frozen samples were thawed quickly in lysis buffer and 1 µM dithiothreitol, and sonicated. Cytoplasmic and nuclear protein fractions were extracted (Pierce Biotechnology). Protein samples (20 µg) and full range molecular weight markers (Amersham Bioscience) were resolved on 10% SDS-PAGE gel, and transferred to Invitrolon PVDF membranes (Invitrogen). The membranes were incubated in Tris-buffer saline (TBS) containing 5% non-fat milk and 0.1% Tween-20 for 1 hour at room temperature to block non-specific binding, and then incubated overnight in appropriate antibody at 4° C. The membranes were washed 3 times, 10 minutes each, in TBS with 0.1% Tween-20, and incubated in peroxidase-conjugated anti-rabbit IgG (1:20,000; Jackson ImmunoResearch) for 1 hour at room temperature. Primary and secondary antibodies were diluted in TBS, 5% non-fat milk and 0.1% Tween-20. Immunoreactivity was visualized using a West Pico Chemiluminescent Kit (Pierce Biotechnology). Digitized images of the films were analyzed using Image Pro-Plus (Media Cybernetics) software.

Antibodies for Western Blot:

Tyrosine hydoxylase (TH) 1:500 (Pelfreeze), β-catenin 1:5000 (BD Biosciences), GSK-3β 1:1000 (Cell Signaling), Ki-67 1:1000 (DAKO). Protein levels were estimated by measuring the optical density of the protein bands using Image Pro-Plus (Media Cybernetics). Briefly, an area of interest (AOI) was sized to incorporate a visible band on the film and then tested against all other visible bands to ensure that each band would be incorporated by the AOI. The density of each band was determined by the Image Pro-Plus software, and a background reading taken using the same AOI. In cases where a band was not obviously visible, the probable location of the band was estimated from adjacent visible bands. Protein levels are reported as the ratio of target protein to actin protein.

Immunohistochemistry:

NT2 11 DISC re-plated spheres in 35 mm poly-1-lysine (sigma) coated plates in DMEM/F12, 10% FBS and 0.1% gentamycin, and then fixed in 4% paraformaldehyde. The re-plated NT2 11 DISC spheres and the undifferentiated NT2 cells were blocked in 10% goat serum for 1 hour at room temperature. Appropriate primary antibodies were incubated overnight at 4° C. The following day, cells were washed 3 times and incubated with goat anti-mouse Alexa 488 (Molecular probes) 1:200, or goat anti-rabbit conjugated to Alexa 594 (Molecular probes) 1:200 for 1 hr at room temperature. Cells were washed 3 times, coverslipped with Vectashield containing DAPI (Vector Laboratories Inc.) and examined under epifluorescence.

Antibodies for Immunohistochemistry:

Tyrosine hydroxylase (TH) 1:400 (Pel Freeze), MAP-2 1:500 (Chemicon), synaptophysin 1:1500 (Chemicon).

RT-PCR:

Total RNA was isolated from undifferentiated NT2 cells, NT2 spheres and re-plated NT2 using TRI Reagent (Sigma) followed by cDNA synthesis from 5 µg of total RNA using SuperScript First strand synthesis (Invitrogen). The following PCR conditions were optimized as shown: GAPDH (5' accacagtccatgccatcac 3',5' tccaccaccctgttgctgta 3'; 30 cycles, 60° C.) [Megiorni F, B Mora, P Indovina and M C Mazzilli. (2005)], TH (5' tgtcagagctggacaagtgt 3', 5' gatattgtcttcccggtagc 3'; 33 cycles, 58° C.) [Long X, M Olszewski, W Huang and M Kletzel. (2005)], Nurr1 (5' ttctccttaagcaatcgccc 3', 5' aagccttttgcagccctcacag 3', 35 cycles, 60° C.), Engrailed-1 En-1 (5'gcaaccccggctatcctactatg 3', 5' atgtagcggtttgcctggaac 3', 35 cycles, 60° C.), Lmx1b (5' acgaggagtgtttgcagtgcg 3', 5 ccctccttgagcacgaattcg 3', 30 cycles, 60° C.) [Park C H, Y K Minn, J Y Lee, D H Choi, M Y Chang, J W Shim, J Y Ko, H C Koh, M J Kang, J S Kang, D J Rhie, YS Lee, H Son, S Y Moon, K S Kim and S H Lee. (2005)], Pitx3 (5' actaggcccta- cacac 3', 5 tttttttgacagtccgc 3', 30 cycles, 55° C.) [Zeng X, J Cai, J Chen, Y Luo, Z B You, E Fotter, Y Wang, B Harvey, T Miura, C Backman, G J Chen, M S Rao and W J Freed. (2004)]. Digitized images of the films were analyzed using Image Pro-Plus (Media Cybernetics, Silver Springs, Md.) software. The level of mRNA was estimated by measuring the optical density of mRNA bands using Image Pro-Plus (Media Cybernetics) as mentioned above.

Methodology for Cell Production

1. Expanding the NT2 cells in conventional culture in DMEM F12 (which is used in all subsequent cultures, as well)

2. Lift and grow the NT2 cells in suspension culture for 11 days. The 3-dimensional adhesion of the cells seems to trigger the differentiation process. Previous reports have stated that the NT2 cells do not differentiate after 7 days in suspension culture. However we have noticed that, at the time periods we use, there is some differentiation.

3. Replate the cells on laminin (also works on PLL, although laminin is preferred) and grow for 14 days. This is the step where the differentiation is observed to proceed most dramatically. A 4-fold increase in dopaminergic neurons has been observed at this step, as compared to the 11 day spheres. Additionally, while there are NT2 cells that have not differentiated and are still dividing, within the replated cells, all the differentiated cells (dopaminergic, cholinergic, GABAergic and glutamatergic) are postmitotic. Sorting methods are being developed to sort the differentiated neurons from the NT2 cells that are still in the cell cycle.

The invention is based upon the unexpected observation that purported cancer stem cells within a cancer cell line would respond to this method of differentiation. This technique extends previous techniques used to differentiate neural stem cells to neurons. Some important differences include the time points and the medium used in the instant technique. The instant technique does not rely on neural basal medium. Additionally, the cells are cultured in suspension culture and the replate duration is longer than techniques used for differentiation of neural stem cells.

Example 4

Neuronal Markers Expression

Figure 17:
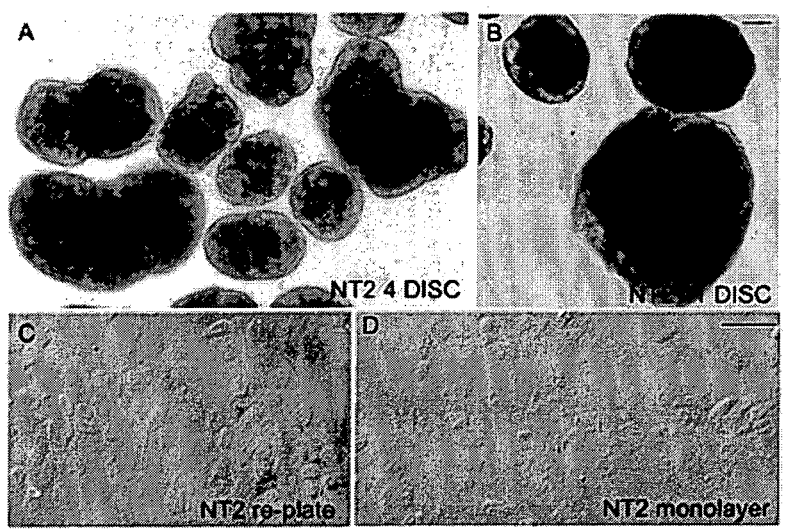
FIG. 17 is a photomicrograph showing formation of NT2 spheres in 3-dimensional suspension culture. (A) NT2 cells forms spheres after 4 days in suspension culture (DISC). (B) NT2 spheres after 11 DISC. (C) 11 DISC NT2 spheres were re-plated for an additional 11 days as a monolayer. (D) Undifferentiated NT2 cells were expanded as a monolayer for 1 week. Scale bar 50 μm.

Cultures of NT2 cells grown in suspension culture without RA remained in suspension with no tendency to form a monolayer (FIG. 17D). NT2 cells tended to adhere to each other, forming aggregates by 4 days (FIG. 17A) that grew larger over time (FIG. 17B). After 11 days in suspension culture, NT2 spheres were re-plated, and NT2N neurons migrated away from the sphere and grew as a monolayer for an additional 11 days (FIG. 17C).

Figure 18:
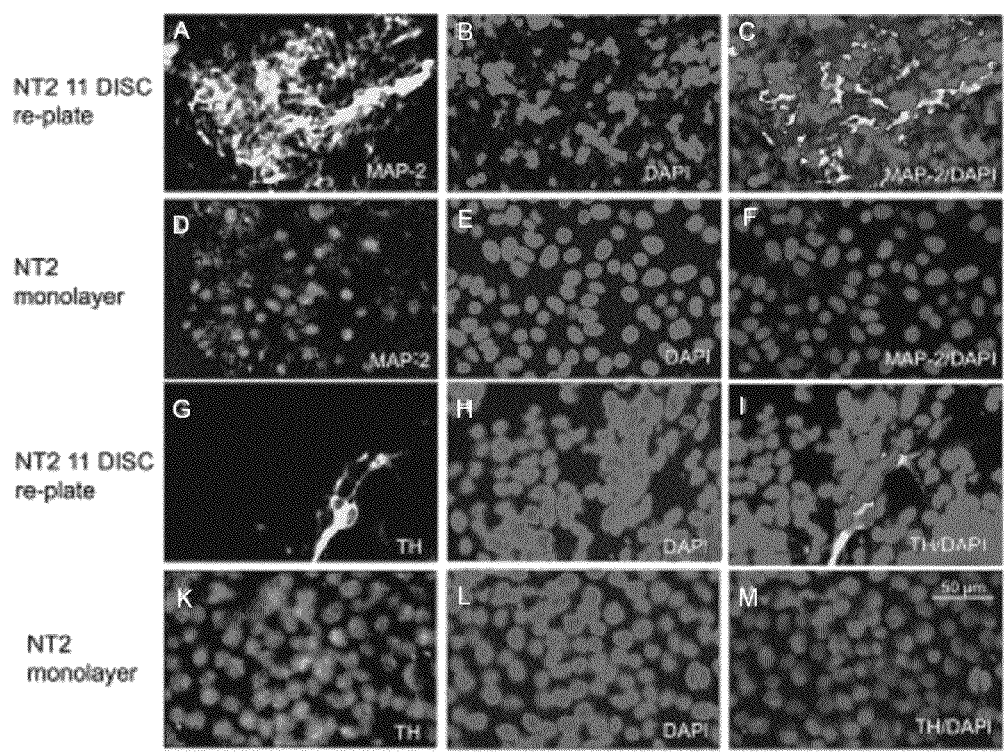
FIG. 18 is a fluorescent photomicrograph of neuronal markers expression by NT2 spheres after re-plate for an additional 11 days as a monolayer. (A) 11 DISC NT2 spheres expressed mature neuronal marker MAP-2 (red), (B) DAPI nuclear stain (blue), (C) double-labeling of MAP-2 and DAPI. (D) Undifferentiated NT2 cells in monolayer did not express MAP-2, (E) DAPI nuclear stain (blue), (F) double-labeling of MAP-2 and DAPI. (G) 11 DISC NT2 sphere expressed TH (red). TH+ cells showed long, extended neurites. (H) DAPI nuclear stain (blue), (I) double-labeling of TH and DAPI. (K) Undifferentiated NT2 cells in monolayer did not show any TH+ cell, (L) DAPI nuclear stain (blue), (M) double-labeling of TH and DAPI. Scale bar 50 μm.
Figure 19:
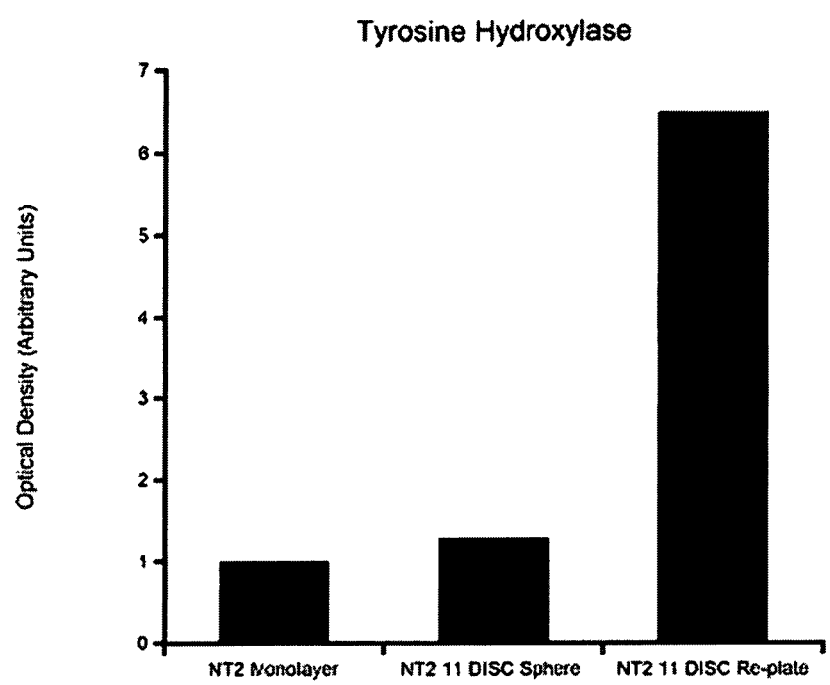
FIG. 19 is a graph illustrating TH expressions in 11 DISC NT2 spheres and 11 DISC re-plate together with undifferentiated NT2 cells in monolayer by western blot analysis. There was no TH expression in the undifferentiated NT2 cells in monolayer. There was 1.2 fold increase in TH expression in 11 DISC NT2 spheres. However, 11 DISC NT2 spheres re-plate showed 6.5 fold increase in the levels of TH expression. Actin was used as a loading control.
Figure 20:
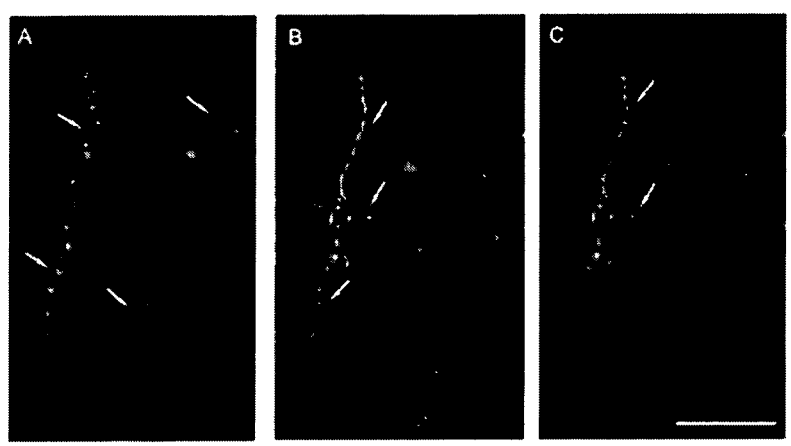
FIG. 20 is fluorescent photomicrograph of NT2 spheres. (A) 11 DISC NT2 sphere after re-plate for an additional 11 days show TH+ cells (red), (B) Neurite outgrowth show immunoreactivity to synaptophysin (green). (C) Double label of TH+ cells showing long, extend synaptophysin+ neurite outgrowth. Scale bar 50 μm.

Immunohistochemistry showed increased expression of the mature neuronal marker MAP-2 in re-plated 11 DISC NT2 spheres (FIGS. 18A and 18C), compared to undifferentiated NT2 monolayer (FIGS. 18D and 18F). Additionally, there was an increase in TH expression in 11 DISC NT2 spheres, compared to undifferentiated NT2 monolayer. When these 11 DISC NT2 spheres were re-plated as a monolayer for an additional 11 days, NT2N neurons showed extended neurites with moderate branching. Additionally, these NT2N neurons expressed TH+ immunoreactivity (FIGS. 18G and 18I) that was still present up to 2 weeks in vitro, unlike hNT cells that lose their TH phenotype within 1 week in vitro [Willing A E, T Zigova, M Milliken, S Poulos, S Saporta, M McGrogan, G Snable and P R Sanberg. (2002)]. Undifferentiated NT2 monolayers showed no TH expression (FIGS. 18K and 18M). Western blot analysis confirmed the increased TH expression in the re-plated NT2 spheres. In 11 DISC re-plated NT2 spheres (FIG. 19) there was a 6.5 fold increase in TH expression (FIG. 19). Furthermore, synaptophysin, a pre-synaptic vesicle protein present in neurons, was expressed in re-plated 11 DISC NT2 spheres (FIG. 20B). TH positive cells (FIG. 20A) were co-localized with synaptophysin (FIG. 20C) indicating possible synapse formation among dopaminergic NT2N neurons in the NT2 spheres. However, synaptophysin positive signal was also evident on some non-TH+ cells.

Example 5

β-Catenin/GSK-3β Expression

Several pathways have been investigated to determine the pathway(s) involved in the differentiation process of NT2N neurons developed in NT2 spheres, including MAPkinase, a known growth and differentiation pathway [Mansour S J, W T Matten, A S Hermann, J M Candia, S Rong, K Fukasawa, G F Vande Woude and N G Ahn. (1994)], and PI3/AKT, a pathway involved in cell proliferation and cell survival [Eves E M, W Xiong, A Bellacosa, S G Kennedy, P N Tsichlis, M R Rosner and N Hay. (1998)]. The Wnt signaling pathway, another pathway involved in cell survival, proliferation and differentiation, has also been implicated (Kikuchi A. (2000)). β-catenin, the cytoplasmic element of Wnt pathway, is involved in adhesion with cadherin and transcription through TCF/LEF transcription complex [Gottardi C J and B M Gumbiner. (2004)]. In 11 DISC re-plated spheres there was a 1.3 and 1.6 fold increase in nuclear β-catenin compared to nuclear β-catenin of undifferentiated NT2 monolayer and NT2 11 DISC, respectively (FIG. 21). Cytoplasmic β-catenin decreased 0.8 fold in NT2 11 DISC and NT2 11 DISC re-plates.

Glycogen synthase kinase-3β phosphorylates β-catenin prior to lysozomal degradation. In our culture conditions, there was a 1.6 fold increase in the phosphorylated (inactive) form of GSK-3 D in 11 DISC NT2 re-plates compared to 11 DISC NT2 spheres (FIG. 21). However, there was essentially no change in the GSK-3β levels between the re-plated NT2 11 DISC spheres and the undifferentiated NT2 monolayer (FIG. 21).

Example 6

Dopaminergic Transcription Expression

Figure 22:
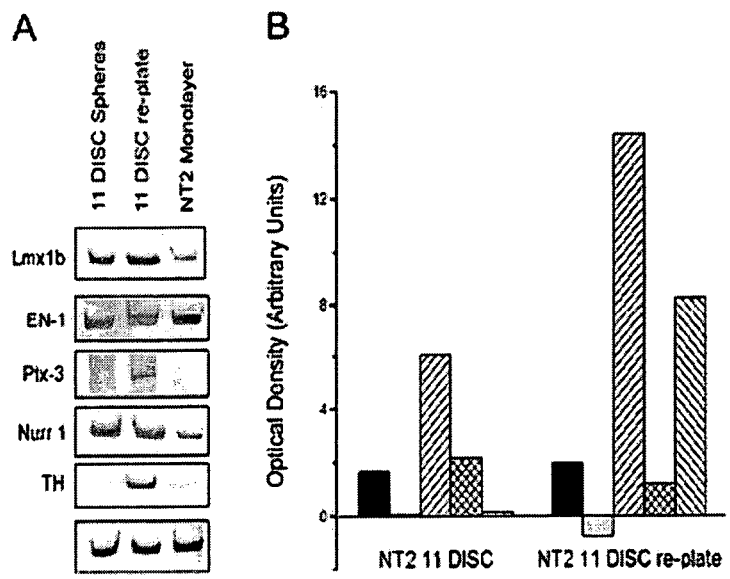
FIG. 22 shows RT-PCR analysis of dopaminergic transcription factors in NT2 cells in monolayer, 11 DISC NT2 spheres and 11 DISC NT2 re-plated spheres. Data in FIG. 22 B are presented as a ratio of transcription factors in 11 DISC spheres and 11 DISC NT2 re-plated spheres compared to levels present in NT2 monolayers. There was a moderate increase in Lmx1b (black bar) in both 11 DISC spheres and re-plates as compared to NT2 monolayers. EN-1 (grey bar) did not change significantly in 11DISC spheres or 11 DISC re-plates. Ptx-3 (right diagonal), which was not present in NT2 monolayers increased 5 fold in NT2 spheres and 16 fold in NT211 DISC re-plate. Nurr1 (cross-hatch) moderately increased in 11 DISC spheres and 11 DISC NT2 re-plated spheres, as compared to NT2 monolayers. Interestingly, TH mRNA (left diagonal) in 11 DISC re-plated spheres increased six fold, as compared to NT2 monolayers, but was moderately increased in 11 DISC spheres. GAPDH was used as a loading control.

RT-PCR analysis showed up-regulated Ptx3 and TH transcription, in the 11 DISC re-plated NT2 spheres compared to undifferentiated NT2 monolayer and 11 DISC NT2 spheres. However, Lmxb1 and Nurrr1 transcription were up-regulated in the both 11 DISC NT2 spheres and the re-plated 11 DISC NT2 spheres compared to undifferentiated NT2 monolayer. There was almost no change in En-1 transcription between all the groups (FIG. 22).

Example 7

Ki-67 Expression

Figure 23:
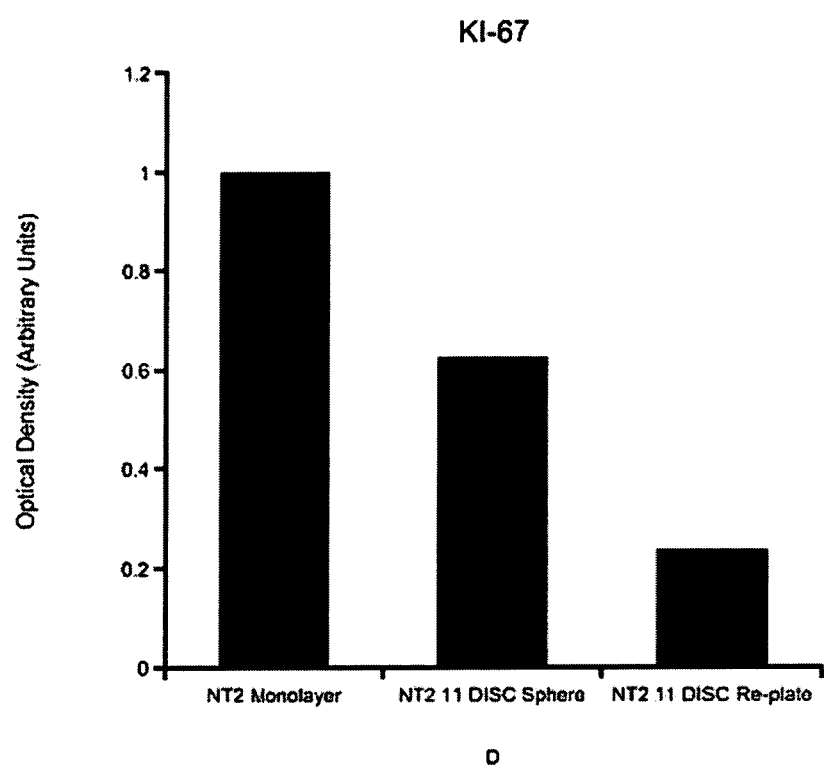
FIG. 23 is a graph illustrating Ki-67 expression in undifferentiated NT2 monolayer, 11 DISC NT2 spheres an 11 DISC NT2 re-plate. There was 1.6 fold decrease in Ki-67 expression in the NT2 11 DISC spheres, while in NT2 11 DISC re-plate there was 5 fold decrease in Ki-67 expression. Actin was used as a loading control.

NT2 11 DISC spheres and NT2 11 DISC re-plate showed 1.6 and 5 fold decreases of nuclear protein Ki-67 expression, respectively, (FIG. 23) compared to the undifferentiated NT2 monolayer suggesting that cell proliferation within the differentiated NT2 11 DISC re-plates has markedly slowed.

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:
1. A method for the stable differentiation of Ntera2/D1 (NT2) cells into neuronal cells expressing Lmx1 b, Pitx3, tyrosine hydroxylase (TH) and Nurr1 in the absence of retinoic acid consisting essentially of the steps of:
expanding NT2 cells in layer culture in the absence of retinoic acid;
subculturing the expanded NT2 cells in the absence of retinoic acid;
growing the subcultured NT2 cells in suspension culture in the absence of retinoic acid and exogenous growth factors for at least 11 days with the medium being changed daily;
replating the cells on an adherent surface;
growing the replated cells for at least 11 days; and
assaying the replated cells to determine expression of mature neuronal markers Lmx1b, Pitx3, tyrosine hydroxylase, and Nurr1;

wherein the replated cells become differentiated neuronal cells as determined by an increased expression of the mature neuronal markers;

whereby the differentiated neuronal cells exhibit a stable neuronal phenotype for longer than 30 days after replating of cells.

2. The method according to claim 1 further comprising assaying the replated cells to determine expression of MAP-2 and synaptophysin.

3. The method according to claim 1 wherein the adherent surface is selected from the group consisting of laminin, poly-L-lysine (PLL) or DLL.

4. A method of generating a non-proliferating, differentiated, mature dopaminergic neuronal cell which expresses Lmx1b, Pitx3, tyrosine hydroxylase, and Nurr1 comprising the steps of:

expanding Ntera2/D1 (NT2) cells in a monolayer culture system in the presence of serum without additional growth factors and in the absence of retinoic acid;

subculturing the expanded NT2 cells in a suspension culture system for at least 11 days in the presence of serum without additional growth factors and in the absence of retinoic acid;

replating the suspended cultured NT2 cells in a monolayer culture system for at least 11 days in the presence of serum without additional growth factors and in the absence of retinoic acid; and assaying the suspended cultured NT2 cells to determine expression of mature neuronal markers Lmx1b, Pitx3, tyrosine hydroxylase, and Nurr1.

* * * * *